(12) United States Patent
Shiraiwa

(10) Patent No.: US 9,891,105 B2
(45) Date of Patent: Feb. 13, 2018

(54) MICROSPECTROSCOPE INCLUDING OPTICAL FIBERS AND SPECTROSCOPE

(71) Applicant: Otsuka Electronics Co., Ltd., Osaka (JP)

(72) Inventor: Hisashi Shiraiwa, Hirakata (JP)

(73) Assignee: Otsuka Electronics Co., Ltd., Osaka (JP)

( * ) Notice: Subject to any disclaimer, the term of this patent is extended or adjusted under 35 U.S.C. 154(b) by 0 days.

(21) Appl. No.: 15/209,843

(22) Filed: Jul. 14, 2016

(65) Prior Publication Data

US 2017/0059407 A1 Mar. 2, 2017

(30) Foreign Application Priority Data

Aug. 31, 2015 (JP) .................................. 2015-170847

(51) Int. Cl.
*G01J 3/28* (2006.01)
*G01J 3/44* (2006.01)
*G02B 21/00* (2006.01)
*G01N 21/64* (2006.01)
*G01N 21/65* (2006.01)
(Continued)

(52) U.S. Cl.
CPC ............... *G01J 3/28* (2013.01); *G01J 3/0208* (2013.01); *G01J 3/0218* (2013.01); *G01J 3/18* (2013.01); *G01J 3/2803* (2013.01); *G01J 3/44* (2013.01); *G01J 3/4406* (2013.01); *G01N 21/6452* (2013.01); *G01N 21/6458* (2013.01); *G01N 21/65* (2013.01); *G02B 21/004* (2013.01); *G02B 21/0032* (2013.01); *G02B 21/0064* (2013.01); *G01N 2021/6484* (2013.01); *G01N 2201/0833* (2013.01); *G01N 2201/0846* (2013.01)

(58) Field of Classification Search
CPC ............... G01N 2201/0826; G01N 2201/0833
See application file for complete search history.

(56) References Cited

U.S. PATENT DOCUMENTS

| 5,615,673 A | 4/1997 | Berger et al. |
| 2001/0052979 A1 | 12/2001 | Treado et al. |

(Continued)

FOREIGN PATENT DOCUMENTS

| EP | 2685304 A1 | 1/2014 |
| GB | 2479012 A | 9/2011 |

(Continued)

OTHER PUBLICATIONS

The extended European search report issued by the European Patent Office on Nov. 30, 2016, which corresponds to European Patent Application No. 16180465.3-1554 and is related to U.S. Appl. No. 15/209,843.

*Primary Examiner* — Shawn Decenzo
(74) *Attorney, Agent, or Firm* — Studebaker & Brackett PC

(57) ABSTRACT

A microspectroscope includes: a light source; a plurality of light projecting optical fibers that receive light from the light source; a spectroscope; a plurality of light receiving optical fibers for guiding received light to the spectroscope; and a confocal optical system for causing each of a plurality of beams from the plurality of light projecting optical fibers to be condensed and irradiated onto a sample, and forming images of a plurality of beams from a plurality of condensing points on the sample, respectively on the plurality of light receiving optical fibers.

6 Claims, 14 Drawing Sheets

(51) Int. Cl.
*G01J 3/02* (2006.01)
*G01J 3/18* (2006.01)

(56) References Cited

U.S. PATENT DOCUMENTS

| | | | |
|---|---|---|---|
| 2008/0029711 | A1 | 2/2008 | Viellerobe et al. |
| 2010/0148073 | A1 | 6/2010 | Nelson et al. |
| 2010/0168586 | A1* | 7/2010 | Hillman ............. G02B 23/2476 600/476 |
| 2010/0265502 | A1* | 10/2010 | Nelson ....................... G01J 3/02 356/317 |
| 2012/0081704 | A1* | 4/2012 | Morrow .................. G02B 6/32 356/302 |

FOREIGN PATENT DOCUMENTS

| | | |
|---|---|---|
| JP | 2009-097772 A | 4/2000 |
| JP | 2006-258990 A | 9/2006 |
| JP | 2012-237647 A | 12/2012 |
| JP | 2014-010216 A | 1/2014 |
| JP | 2014-016531 A | 1/2014 |

\* cited by examiner

MICROSPECTROSCOPE INCLUDING OPTICAL FIBERS AND SPECTROSCOPE

CROSS-REFERENCE TO RELATED APPLICATION

This application is based upon and claims the benefit of priority from Japanese patent application No. 2015-170847, filed on Aug. 31, 2015, the disclosure of which are incorporated herein in its entirety by reference.

BACKGROUND OF THE INVENTION

Field of the Invention

The present invention relates to a microspectroscope, and in particular relates to a microspectroscope for separating light from a plurality of positions on a sample.

Description of Related Art

Recently, multifocal microscopes have been developed in which scanning by an optical system is not required or can be reduced. For example, JP 2014-10216A (Patent Document 1) discloses the following configuration. That is to say, a multifocal confocal microscope includes: an illumination optical system having a two-dimensionally arranged spot-array light source, wherein light from the light source is irradiated onto a sample at positions that are substantially conjugate with the light source; an imaging optical system that forms an image of observation light from the sample, on a pinhole array two-dimensionally arranged at positions that are substantially conjugate with condensing positions on the sample and the spot-array light source; and a detection means for detecting the light forming the image.

Furthermore, JP 2012-237647A (Patent Document 2) discloses the following configuration. That is to say, a multifocal confocal Raman spectroscopic microscope includes: a laser light source that emits excitation light; a microlens array that divides the excitation light from the laser light source into a plurality of narrow beams in a matrix, and condenses each beam; an edge filter that reflects the plurality of beams that have passed through the microlens array and a relay lens; a pinhole array having a plurality of pinholes, wherein the plurality of beams that have passed through the edge filter respectively pass through the pinholes at condensing points; an object lens on which the plurality of beams that have passed through the pinhole array are incident via a relay lens, the object lens for condensing each of the plurality of beams on a sample; a confocal optical system in which, while reflected light of the excitation light and Raman scattered light from the sample return via the object lens, the relay lens, and the pinhole array to the edge filter, the Raman scattered light that has been transmitted through the edge filter is condensed; a fiber bundle constituted by a plurality of optical fibers having incident ends on which a plurality of beams of the Raman scattered light condensed by the confocal optical system are respectively incident, and emission ends that are arranged in one line; a light separating means on which beams from the emission ends of the plurality of optical fibers forming the fiber bundle are incident; and a light receiving means for receiving the beams that have passed through the light separating means.

SUMMARY OF THE INVENTION

There is a demand for techniques for providing devices, the techniques being superior to those described in the above-described Patent Documents.

The present invention was made in order to solve the above-described problem, and it is an object thereof to provide a superior microspectroscope.

(1) An aspect of the present invention is directed to a microspectroscope, including: a light source; a plurality of light projecting optical fibers that receive light from the light source; a spectroscope; a plurality of light receiving optical fibers for guiding received light to the spectroscope; and a confocal optical system for causing each of a plurality of beams from the plurality of light projecting optical fibers to be condensed and irradiated onto a sample, and forming images of a plurality of beams from a plurality of condensing points on the sample, respectively on the plurality of light receiving optical fibers.

In this manner, a multifocal and confocal configuration is realized by paying attention to the use of a plurality of light projecting optical fibers and a plurality of light receiving optical fibers, so that light from a plurality of positions on a sample can be separated with a simple and easily adjustable configuration in which no pinhole array is provided in the optical system, for example. Accordingly, it is possible to provide a superior microspectroscope.

(2) It is preferable that the plurality of light projecting optical fibers and the plurality of light receiving optical fibers are individually two-dimensionally arranged, and at least either the plurality of light projecting optical fibers or the plurality of light receiving optical fibers are arranged closer to each other than in a state in which the optical fibers are arranged in contact with each other in a square lattice, in a cross-section cut along a plane that is orthogonal to an extending direction of the optical fibers.

With this configuration, the number of optical fibers per unit area in the cross-section can be increased, and thus the area of light irradiated by the light source onto the light projecting optical fibers can be made smaller. Accordingly, the amount of light received by one light projecting optical fiber from the light source can be increased, and thus the usage efficiency of light can be improved. Furthermore, the occupancy of the device by the optical fibers can be made smaller.

(3) It is preferable that the microspectroscope further includes: a light projecting marker optical fiber that is fixed along the plurality of light projecting optical fibers and that receives light from a light source, on an input end side of the light projecting optical fibers; and a light receiving marker optical fiber that is fixed along the plurality of light receiving optical fibers and that receives light from a light source, on an output end side of the light receiving optical fibers, and the confocal optical system causes each of a marker beam from the light projecting marker optical fiber and a marker beam from the light receiving marker optical fiber to be condensed and irradiated onto a sample.

With this configuration, based on a relationship between the condensing position of a marker beam from the light projecting marker optical fiber and the condensing position of a marker beam from the light receiving marker optical fiber, a relationship between the condensing positions of beams from the condensing points on the sample and the positions of the light receiving optical fibers can be seen, and whether or not the state of the optical system is suitable can be easily determined. Accordingly, for example, when the state of the optical system is not suitable, the arrangement of the optical elements in the optical system can be altered so that the state of the optical system can be kept suitable.

(4) It is more preferable that the microspectroscope further includes: a light projecting marker light source; and a light receiving marker light source; the light projecting marker optical fiber receives light from the light projecting marker light source, on an input end side of the light projecting optical fibers, the light receiving marker optical fiber receives light from the light receiving marker light source, on an output end side of the light receiving optical fibers, and the light projecting marker light source and the light receiving marker light source output light having mutually different colors.

With this configuration, marker beams having mutually different colors from the light projecting marker optical fiber and the light receiving marker optical fiber can be irradiated onto the sample, and thus whether or not the state of the optical system is suitable can be more easily determined.

(5) It is preferable that the microspectroscope includes a plurality of said light sources, the plurality of light projecting optical fibers receive light from the plurality of light sources, each of the light sources irradiates light onto one or a plurality of corresponding light projecting optical fibers, which are part of the plurality of light projecting optical fibers, and optical paths of light from the light sources are regulated such that light that is received by each light projecting optical fiber is light from one corresponding light source.

With this configuration, the number of light projecting optical fibers that are targets of irradiation by one light source can be reduced, and thus the intensity of light received by each light projecting optical fiber from the light source can be increased. Accordingly, light from the condensing points on the sample can be more suitably separated. Furthermore, one light projecting optical fiber can be prevented from receiving light from a plurality of light sources, and thus each condensing point on the sample can be irradiated with light from a single light source. Accordingly, spectral results of light from the condensing points on the sample can be prevented from reflecting variations between the light sources in spectral characteristics of light irradiated from the light sources.

(6) It is preferable that an outer diameter of a core of each of the light receiving optical fibers is larger than an outer diameter of a core of each of the light projecting optical fibers.

With this configuration, the margin for displacement between the condensing positions of beams from the condensing points on the sample and the center positions of the cores of the light receiving optical fibers can be more reliably ensured.

(7) Another aspect of the present invention is directed to a microspectroscope, including: one or a plurality of light sources; a spectroscope; a plurality of light receiving optical fibers that are two-dimensionally arranged, for guiding received light to the spectroscope; and a confocal optical system for causing each of a plurality of beams formed by light from the light source to be condensed and irradiated onto a sample, and forming images of a plurality of beams from a plurality of condensing points on the sample, respectively on the plurality of light receiving optical fibers, wherein the plurality of light receiving optical fibers are two-dimensionally arranged, and are arranged closer to each other than in a state in which the optical fibers are arranged in contact with each other in a square lattice, in a cross-section cut along a plane that is orthogonal to an extending direction of the optical fibers, the microspectroscope further includes a plurality of light receiving marker optical fibers that are fixed along the plurality of light receiving optical fibers and that receive light from the light source, on an output end side of the light receiving optical fibers, and the confocal optical system causes each of a plurality of marker beams from the plurality of light receiving marker optical fibers to be condensed and irradiated onto the sample.

With this configuration, for example, based on a relationship between the condensing positions of a plurality of marker beams formed by light from the light source and the condensing positions of marker beams from the plurality of light receiving marker optical fibers, a relationship between the condensing positions of beams from the condensing points on the sample and the positions of the light receiving optical fibers can be seen, and whether or not the state of the optical system is suitable can be easily determined, with a simple and easily adjustable configuration. Accordingly, for example, when the state of the optical system is not suitable, the arrangement of the optical elements in the optical system can be altered so that the state of the optical system can be kept suitable. Furthermore, the occupancy of the device by the light receiving optical fibers can be made smaller. Accordingly, it is possible to provide a superior microspectroscope.

According to the present invention, it is possible to provide a superior microspectroscope.

The foregoing and other objects, features, aspects and advantages of the present invention will become more apparent from the following detailed description of the present invention when taken in conjunction with the accompanying drawings.

DETAILED DESCRIPTION OF THE INVENTION

Figure 1:
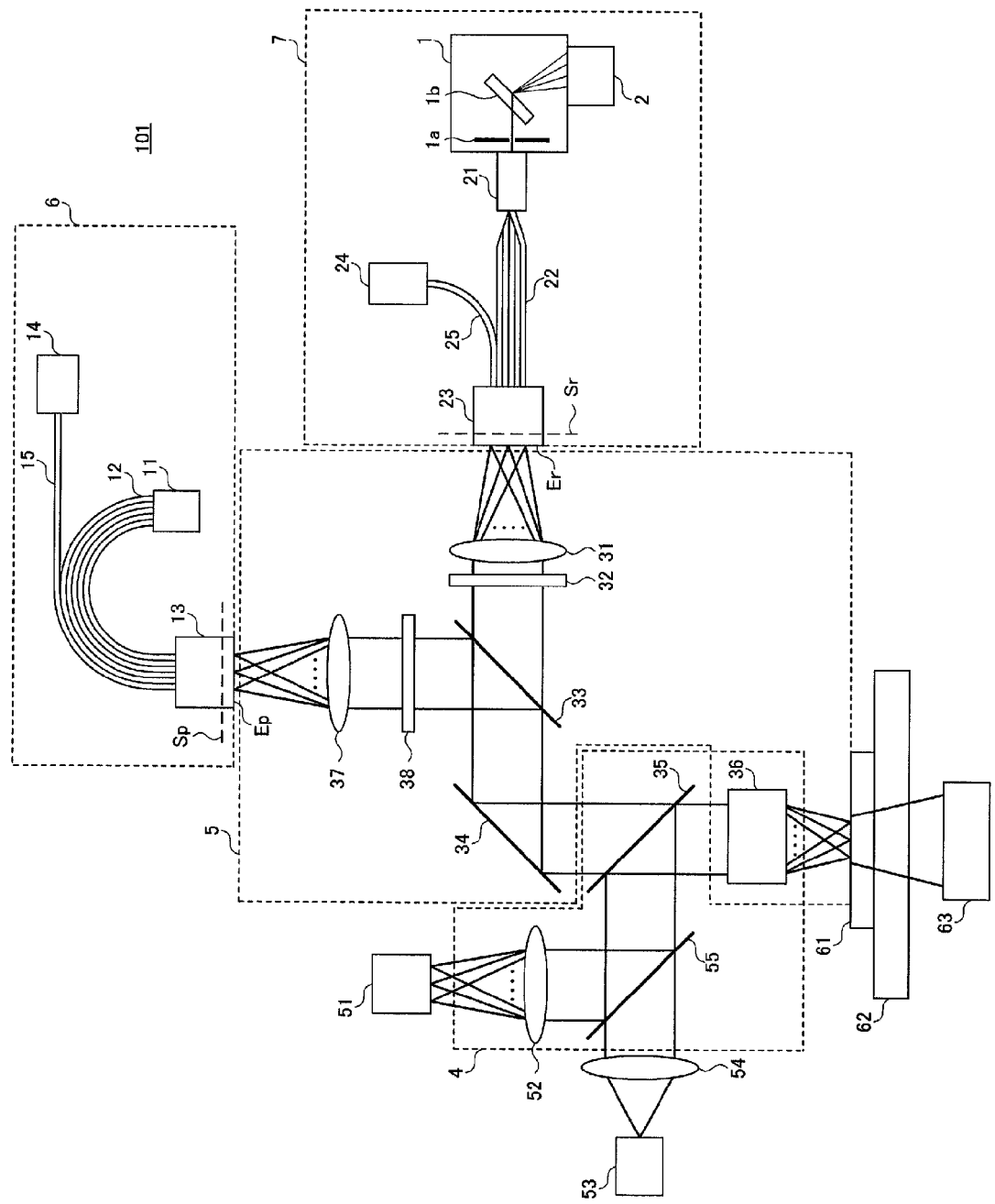
FIG. 1 is a view showing the configuration of a microspectroscope according to a first embodiment of the present invention.

Hereinafter, embodiments of the present invention will be described with reference to the drawings. Note that the same or corresponding constituent elements in the drawings are denoted by the same reference numerals, and a description thereof is not repeated. Furthermore, at least part of the embodiments described below may be freely combined.
First Embodiment FIG. 1 is a view showing the configuration of a microspectroscope according to the first embodiment of the present invention.

Referring to FIG. 1, a microspectroscope 101 includes an observation optical system 4, a confocal optical system 5, a light projecting portion 6, a light receiving portion 7, an observation camera 51, a reflection illuminator 53, a collimating lens 54, an XYZ stage 62, and a transmission illuminator 63.

The observation optical system 4 includes a movable half mirror 35, an object lens 36, an imaging lens 52, and a half mirror 55.

The light projecting portion 6 includes a measurement light source 11, a plurality of light projecting optical fibers 12, a light projecting-side two-dimensional array fixing portion 13, a light projecting marker light source 14, and a light projecting marker optical fiber 15.

The light receiving portion 7 includes a spectroscope 1, a two-dimensional detector 2, a light receiving-side one-dimensional array fixing portion 21, a plurality of light receiving optical fibers 22, a light receiving-side two-dimensional array fixing portion 23, a light receiving marker light source 24, and a light receiving marker optical fiber 25.

In this example, the light projecting portion 6 is provided with, for example, 36 light projecting optical fibers 12 and four light projecting marker optical fibers 15. The light receiving portion 7 is provided with, for example, 36 light receiving optical fibers 22 and four light receiving marker optical fibers 25.

The confocal optical system 5 includes a condensing lens 31, a band-stop filter 32, a dichroic mirror 33, a scanning mirror 34, the object lens 36, a collimating lens 37, and a band-pass filter 38.

The light projecting optical fibers 12 respectively have input ends facing the measurement light source 11 and output ends facing the collimating lens 37. The light receiving optical fibers 22 respectively have input ends facing the condensing lens 31 and output ends facing the spectroscope 1.

The light projecting marker optical fibers 15 respectively have input ends facing the light projecting marker light source 14 and output ends facing the collimating lens 37. The light receiving marker optical fibers 25 respectively have input ends facing the light receiving marker light source 24 and output ends facing the condensing lens 31.

The measurement light source 11 is, for example, a light source that generates light, and is specifically a laser that outputs light having a single color. The measurement light source 11 may be an LED (light-emitting diode) that outputs light having a wide bandwidth, an incandescent electric lamp, or the like.

The light projecting optical fibers 12 receive light from the measurement light source 11 on the input end side of the light projecting optical fibers 12, and transmit the received light to irradiate the collimating lens 37.

The light projecting marker light source 14 is, for example, an LED, an incandescent electric lamp, or the like. The light projecting marker light source 14 may be a laser.

The light projecting marker optical fibers 15 are fixed along the light projecting optical fibers 12, receive light from the light projecting marker light source 14, on the input end side of the light projecting optical fibers 12, and transmit the received light to irradiate the collimating lens 37.

Figure 2:
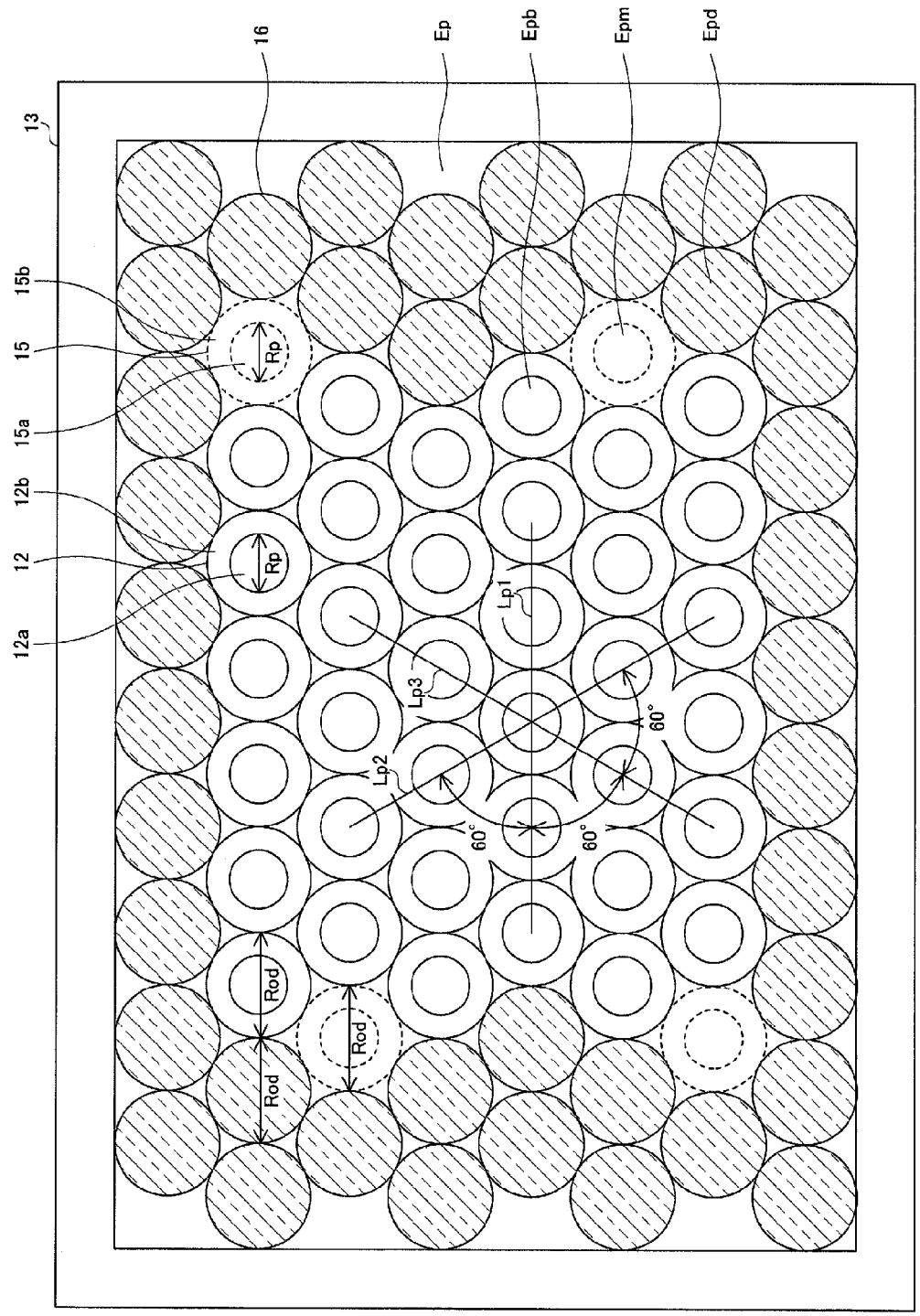
FIG. 2 is a view showing an example of end faces of fibers at a light projecting-side two-dimensional array fixing portion of the microspectroscope according to the first embodiment of the present invention.

FIG. 2 is a view showing an example of end faces of fibers at the light projecting-side two-dimensional array fixing portion of the microspectroscope according to the first embodiment of the present invention.

FIG. 2 is a plan view in a direction toward end faces Epb of the output ends of the 36 light projecting optical fibers 12, showing the end faces Epb, end faces Epm of the output ends of the four light projecting marker optical fibers 15, and end faces Epd of 40 dummy fibers 16.

In this drawing, for easy distinction, the end faces Epb of the light projecting optical fibers 12 and the end faces Epm of the light projecting marker optical fibers 15 are respectively represented by solid lines and broken lines, and the end faces Epd of the dummy fibers 16 are hatched.

The fibers in the light projecting portion 6 are, for example, such that the end faces Epb are aligned in line with a plane (hereinafter, also referred to as a light projecting end face Ep) that includes the end faces Epb and that is orthogonal to the extending direction of the light projecting optical fibers 12, and the end faces Epm and Epd are aligned in line with the light projecting end face Ep.

Furthermore, the cross-sections of the light projecting optical fibers 12, the light projecting marker optical fibers 15, and the dummy fibers 16 are, for example, in the shape of circles. Note that the cross-sections of the fibers do not necessarily have to be in the shape of circles, and may be in the shape of polygons.

Referring to FIG. 2, each light projecting optical fiber 12 includes a core 12a and a clad 12b. The light projecting optical fiber 12 has an outer diameter Rod of, for example, 250 μm. The core 12a has an outer diameter Rp of for example, 150 μm.

Each light projecting marker optical fiber 15 includes a core 15a and a clad 15b. The light projecting marker optical fiber 15 has an outer diameter that is, for example, Rod that is the same as the outer diameter of the light projecting optical fiber 12, that is, 250 μm. The core 15a has an outer diameter that is, for example, Rp that is the same as the outer diameter of the core 12a of the light projecting optical fiber 12, that is, 150 μm.

Each dummy fiber 16 has an outer diameter that is, for example, Rod that is the same as the outer diameter of the light projecting optical fiber 12, that is, 250 μm.

The light projecting optical fibers 12, the light projecting marker optical fibers 15, and the dummy fibers 16 are, for example, individually two-dimensionally arranged.

For example, in a cross-section Sp cut along a plane that is orthogonal to the extending direction of the light projecting optical fibers 12, the light projecting optical fibers 12 are arranged closer to each other than in a state in which the light projecting optical fibers 12 are arranged in contact with each other in a square lattice. In this example, the light projecting optical fibers 12 are arranged, for example, so as to extend in the same direction.

In other words, for example, in a plan view in a direction toward the end faces Epb of the light projecting optical fibers 12, the light projecting optical fibers 12 are arranged closer to each other than in a state in which the light projecting optical fibers 12 are arranged in contact with each other in a square lattice.

For example, if the cross-section Sp is positioned near the light projecting end face Ep as shown in FIG. 1, the cross-section Sp is similar to the light projecting end face Ep shown in FIG. 2.

Figure 3:
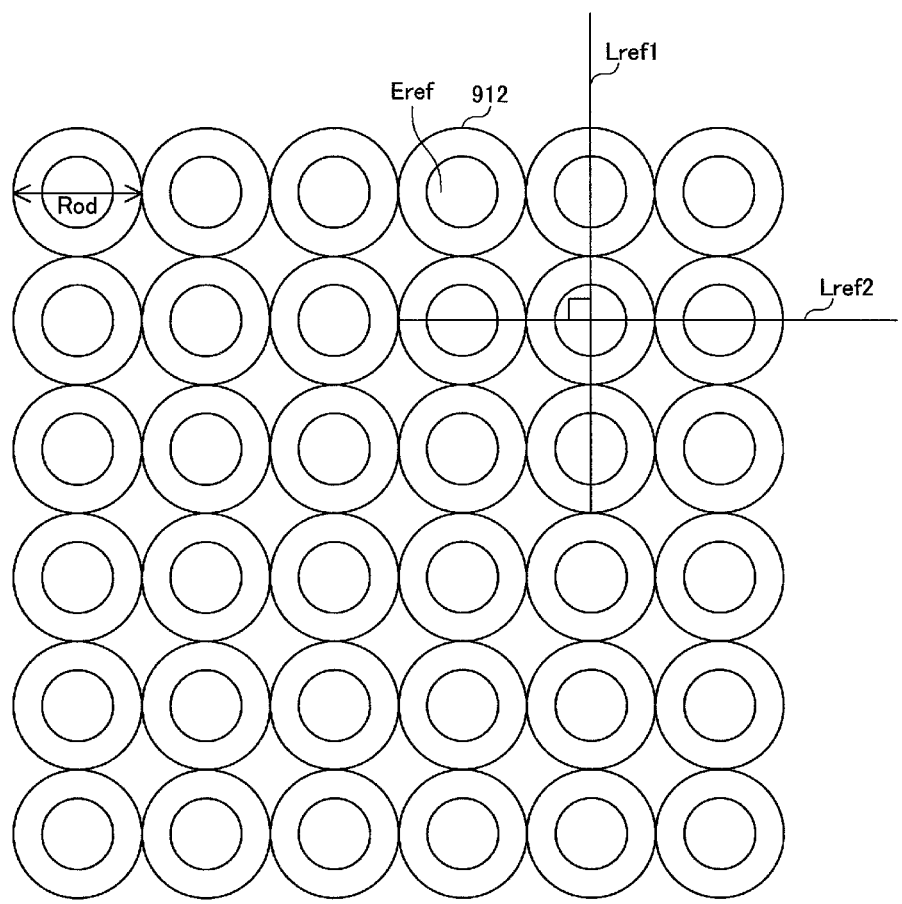
FIG. 3 is a view showing an example of end faces of fibers according to a comparative example.

FIG. 3 is a view showing an example of end faces of fibers according to a comparative example. FIG. 3 is a plan view in a direction toward end faces Eref of 36 optical fibers 912, showing the end faces Eref.

The optical fibers 912 are arranged in contact with each other in a square lattice. The state of being "arranged in a square lattice" refers to, for example, an arrangement as shown in FIG. 3 in which any optical fiber 912 is arranged in contact with the closest other optical fibers 912 arranged along a straight line Lref1 that extends through the center of the optical fiber 912, and with the closest other optical fibers 912 arranged along a straight line Lref2 that is orthogonal to the straight line Lref1 at the center.

Again referring to FIG. 2, specifically, for example, in a plan view in a direction toward the cross-section Sp or the end faces Epb, the light projecting optical fibers 12 are arranged in contact with each other in an equilateral triangle lattice, that is, they are arranged closest to each other. In other words, for example, in a plan view in a direction toward the cross-section Sp or the end faces Epb, the light projecting optical fibers 12 are arranged in contact with six other fibers such as the light projecting optical fibers 12.

The state of being "arranged in an equilateral triangle lattice" refers to, for example, an arrangement as shown in FIG. 2 in which any light projecting optical fiber 12 is arranged in contact with the closest other light projecting optical fibers 12 arranged along a straight line Lp1 that extends through the center of the light projecting optical fiber 12, with the closest other light projecting optical fibers 12 arranged along a straight line Lp2 that intersects the straight line Lp1 at 60 degrees at the center, and with the closest other light projecting optical fibers 12 arranged along a straight line Lp3 that intersects each of the straight lines Lp1 and Lp2 at 60 degrees at the center.

In the arrangement shown in FIG. 3, for example, if each optical fiber 912 and each light projecting optical fiber 12 have the same outer diameter Rod, the number of optical fibers 912 per unit area is 1/(Rod×Rod).

On the other hand, in the arrangement shown in FIG. 2, for example, the number of light projecting optical fibers 12 per unit area is $(2/\sqrt{3}) \times (Rod \times Rod) = 1.15/(Rod \times Rod)$.

Accordingly, in the light projecting end face Ep shown in FIG. 2 or the cross-section Sp, the light projecting optical fibers 12 are arranged closer to each other by about 15% than in a state in which they are arranged in contact with each other in a square lattice as shown in FIG. 3.

Although the light projecting optical fibers 12 are arranged in contact with each other in an equilateral triangle lattice in the cross-section Sp in FIG. 2, it is sufficient that, in the cross-section Sp, the light projecting optical fibers 12 are arranged closer to each other than in a state in which they are arranged in contact with each other in a square lattice, as described above. Specifically, for example, it is sufficient that any light projecting optical fiber 12 is arranged in contact with the closest other light projecting optical fibers 12 arranged along a straight line that extends through the center of the light projecting optical fiber 12, and with the closest other light projecting optical fibers 12 arranged along a straight line that intersects the straight line at an angle smaller than 90° and larger than 60° at the center.

Referring to FIG. 2, for example, the 36 light projecting optical fibers 12, the four light projecting marker optical fibers 15, and the 40 dummy fibers 16 are fixed in one piece by the light projecting-side two-dimensional array fixing portion 13.

More specifically, the 36 light projecting optical fibers 12 are bundled in one piece, for example, such that six layers each including six light projecting optical fibers 12 are stacked. Furthermore, the light projecting optical fibers 12 are two-dimensionally arranged, for example, such that their output ends have two-fold symmetry.

The four light projecting marker optical fibers 15 are arranged, for example, at substantially four corners of the 36 light projecting optical fibers 12 bundled in one piece such that the two-fold symmetry is maintained.

The 40 dummy fibers 16 are arranged, for example, between the light projecting optical fibers 12 or the light projecting marker optical fibers 15 and the light projecting-side two-dimensional array fixing portion 13.

With the configuration in which any light projecting optical fiber 12, light projecting marker optical fiber 15, or dummy fiber 16 is arranged in contact with six other fibers in this manner, the centers of the fibers can be stably fixed at the locations of the vertices of equilateral triangles, and thus the center positions of the fibers can be prevented from being displaced from their design positions.

Note that the number of dummy fibers 16 is not limited to 40, and any number is possible as long as at least one layer of the dummy fibers 16 can be arranged between the light projecting optical fibers 12 or the light projecting marker optical fibers 15 and the light projecting-side two-dimensional array fixing portion 13.

Although a case was described in which the cross-sections of the light projecting optical fibers 12, the light projecting marker optical fibers 15, and the dummy fibers 16 are in the shape of circles, even in a case where the cross-sections of the fibers are in the shape of hexagons or the like, the fibers are arranged closer to each other than in a state where they are arranged in contact with each other in a square lattice, in the cross-section Sp.

Again referring to FIG. 1, the confocal optical system 5 has a function of causing each of a plurality of beams from the plurality of light projecting optical fibers 12 to be condensed and irradiated onto a sample 61, and forming images of a plurality of beams from condensing points of the plurality of beams on the sample 61, respectively on the plurality of light receiving optical fibers 22.

More specifically, the collimating lens 37 converts, for example, light spread apart from the output ends of the light projecting optical fibers 12, into a projecting beam group consisting of substantially parallel beams.

Among wavelength components of laser light contained in the projecting beam group from the collimating lens 37, the band-pass filter 38 attenuates, for example, wavelength components other than those at peaks in spectra of the laser light.

The projecting beam group transmitted through the band-pass filter 38 is, for example, reflected by the dichroic mirror 33 and the scanning mirror 34, and is incident on the object lens 36.

The object lens 36 condenses, for example, each of a plurality of beams contained in the projecting beam group reflected by the scanning mirror 34, on the sample 61.

Figure 4:
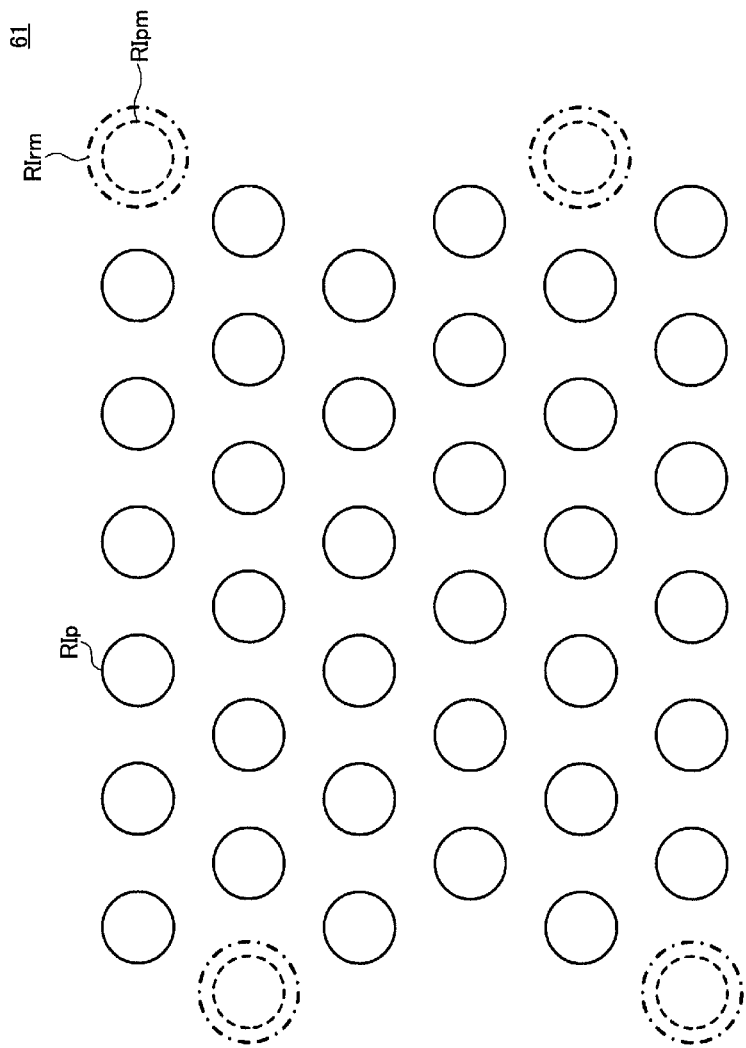
FIG. 4 is a view showing an example of real images formed on a sample in the microspectroscope according to the first embodiment of the present invention.

FIG. 4 is a view showing an example of real images formed on a sample in the microspectroscope according to the first embodiment of the present invention.

In FIG. 4, real images RIp, real images RIpm, and real images RIrm are respectively represented by solid lines, broken lines, and dashed dotted lines.

Referring to FIG. 4, the real images RIp are, for example, real images of the output ends of the cores 12a of the 36 light projecting optical fibers 12, generated by causing each of beams from the output ends of the cores 12a to be condensed on the sample 61 by the confocal optical system 5.

Again referring to FIG. 1, the object lens 36 converts, for example, light spread apart from the real images Rip, into a receiving beam group consisting of substantially parallel beams.

The scanning mirror 34 reflects, for example, the receiving beam group converted by the object lens 36.

Among wavelength components of light contained in the receiving beam group reflected by the scanning mirror 34, the band-stop filter 32 attenuates, for example, wavelength components at peaks in spectra of the laser light of the measurement light source 11.

The condensing lens 31 condenses, for example, each of a plurality of beams contained in the receiving beam group transmitted through the band-stop filter 32.

Figure 5:
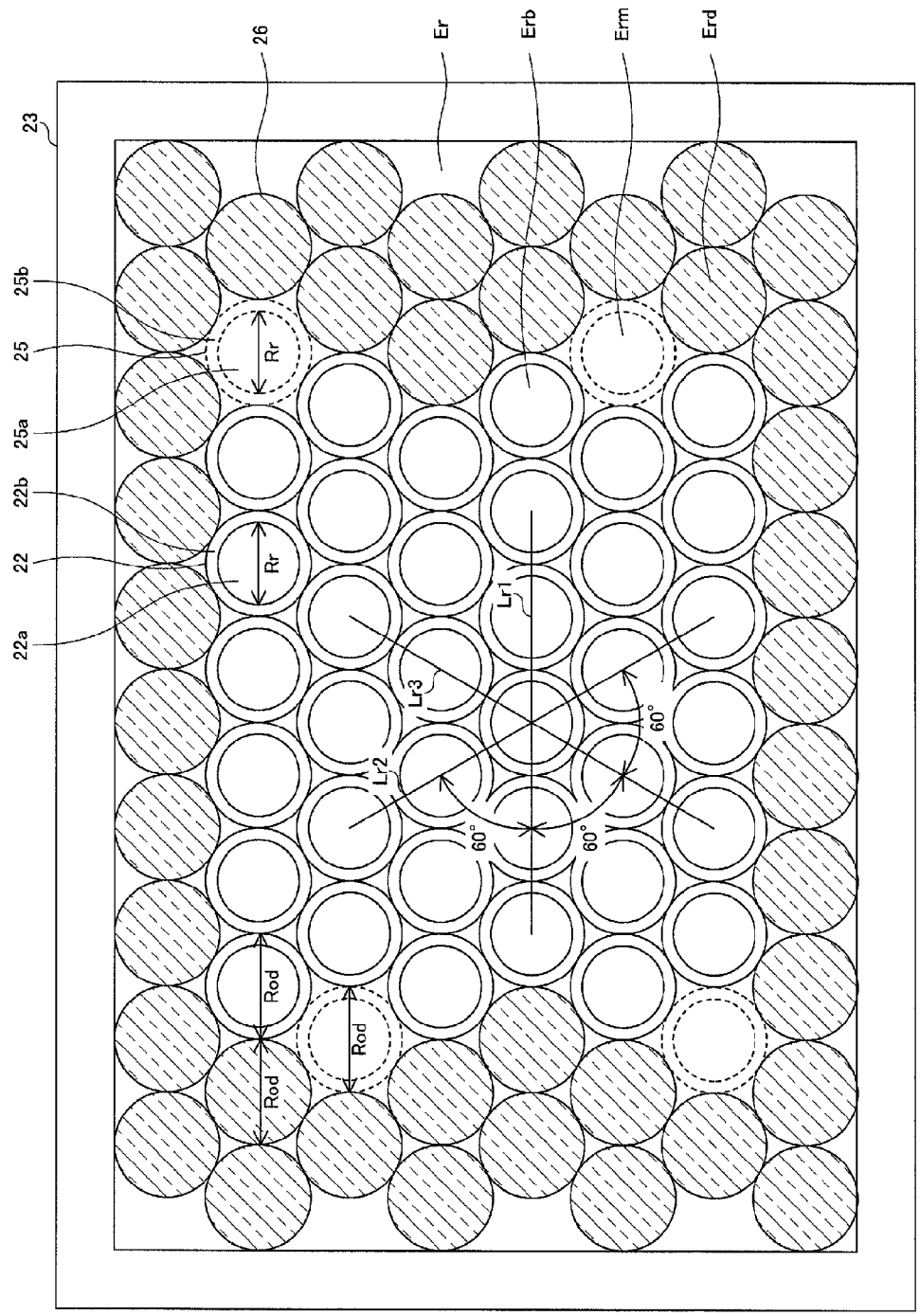
FIG. 5 is a view showing an example of end faces of fibers at a light receiving-side two-dimensional array fixing portion of the microspectroscope according to the first embodiment of the present invention.

FIG. 5 is a view showing an example of end faces of fibers at a light receiving-side two-dimensional array fixing portion of the microspectroscope according to the first embodiment of the present invention.

FIG. 5 is a plan view in a direction toward end faces Erb of input ends of the 36 light receiving optical fibers 22, showing the end faces Erb, end faces Erm of the output ends of the four light receiving marker optical fibers 25, and end faces Erd of 40 dummy fibers 26.

In this drawing, for easy distinction, the end faces Erb of the light receiving optical fibers 22 and the end faces Erm of the light receiving marker optical fibers 25 are respectively represented by solid lines and broken lines, and the end faces Erd of the dummy fibers 26 are hatched.

The fibers in the light receiving portion 7 are, for example, such that the end faces Erb are aligned in line with a plane (hereinafter, also referred to as a light receiving end face Er) that includes the end faces Erb and that is orthogonal to the extending direction of the light receiving optical fibers 22, and the end faces Erm and Erd are aligned in line with the light receiving end face Er.

Furthermore, the cross-sections of the light receiving optical fibers 22, the light receiving marker optical fibers 25, and the dummy fibers 26 are, for example, in the shape of circles. Note that the cross-sections of the fibers do not necessarily have to be in the shape of circles, and may be in the shape of polygons.

Referring to FIG. 5, each light receiving optical fiber 22 includes a core 22a and a clad 22b. The light receiving optical fiber 22 has an outer diameter that is, for example, Rod that is the same as the outer diameter of the light projecting optical fiber 12, that is, 250 μm.

The core 22a of the light receiving optical fiber 22 has an outer diameter Rr that is, for example, larger than the outer diameter Rp of the core 12a of the light projecting optical fiber 12. Specifically, the outer diameter Rr is, for example, 200 μm.

Each light receiving marker optical fiber 25 includes a core 25a and a clad 25b. The light receiving marker optical fiber 25 has an outer diameter that is, for example, Rod that is the same as the outer diameter of the light receiving optical fiber 22, that is, 250 μm. The core 25a has an outer diameter that is, for example, Rr that is the same as the outer diameter of the core 22a of the light receiving optical fiber 22, that is, 200 μm.

Each dummy fiber 26 has an outer diameter that is, for example, Rod that is the same as the outer diameter of the light receiving optical fiber 22, that is, 250 μm.

The light receiving optical fibers 22, the light receiving marker optical fibers 25, and the dummy fibers 26 are, for example, individually two-dimensionally arranged.

For example, in a cross-section Sr cut along a plane that is orthogonal to the extending direction of the light receiving optical fibers 22, the light receiving optical fibers 22 are arranged closer to each other than in a state in which the light receiving optical fibers 22 are arranged in contact with each other in a square lattice. In this example, the light receiving optical fibers 22 are arranged, for example, so as to extend in the same direction.

In other words, for example, in a plan view in a direction toward the end faces Erb of the light receiving optical fibers 22, the light receiving optical fibers 22 are arranged closer to each other than in a state in which the light receiving optical fibers 22 are arranged in contact with each other in a square lattice.

For example, if the cross-section Sr is positioned near the light receiving end face Er as shown in FIG. 1, the cross-section Sr is similar to the light receiving end face Er shown in FIG. 5.

Specifically, for example, in a plan view in a direction toward the cross-section Sr or the end faces Erb, the light receiving optical fibers 22 are arranged in contact with each other in an equilateral triangle lattice, that is, they are arranged closest to each other. In other words, for example, in a plan view in a direction toward the cross-section Sr or the end faces Erb, the light receiving optical fibers 22 are arranged in contact with six other fibers such as the light receiving optical fibers 22.

The state of being "arranged in an equilateral triangle lattice" refers to, for example, an arrangement as in the case of the light projecting optical fibers 12, in which any light receiving optical fiber 22 is arranged in contact with the closest other light receiving optical fibers 22 arranged along a straight line Lr1 that extends through the center of the light receiving optical fiber 22, with the closest other light receiving optical fibers 22 arranged along a straight line Lr2 that intersects the straight line Lr1 at 60 degrees at the center, and with the closest other light receiving optical fibers 22 arranged along a straight line Lr3 that intersects each of the straight lines Lr1 and Lr2 at 60 degrees at the center.

Furthermore, as in the case of the light projecting optical fibers 12, for example, in the light receiving end face Er shown in FIG. 5 or the cross-section Sr, the light receiving optical fibers 22 are arranged closer to each other by about 15% than in a state in which they are arranged in contact with each other in a square lattice.

Although the light receiving optical fibers 22 are arranged in contact with each other in an equilateral triangle lattice in the cross-section Sr in FIG. 5, it is sufficient that, in the cross-section Sr, the light receiving optical fibers 22 are arranged closer to each other than in a state in which they are arranged in contact with each other in a square lattice, as described above. Specifically, for example, it is sufficient that any light receiving optical fiber 22 is arranged in contact with the closest other light receiving optical fibers 22 arranged along a straight line that extends through the center of the light receiving optical fiber 22, and with the closest other light receiving optical fibers 22 arranged along a straight line that intersects the straight line at an angle smaller than 90° and larger than 60° at the center.

For example, the 36 light receiving optical fibers 22, the four light receiving marker optical fibers 25, and the 40 dummy fibers 26 are fixed in one piece by the light receiving-side two-dimensional array fixing portion 23.

More specifically, the 36 light receiving optical fibers 22 are bundled in one piece, for example, such that six layers each including six light receiving optical fibers 22 are stacked. Furthermore, the light receiving optical fibers 22 are two-dimensionally arranged, for example, such that their input ends have two-fold symmetry.

Furthermore, the 36 light receiving optical fibers 22 are bundled in one piece, for example, such that the centers of the 36 light receiving optical fibers 22 and the centers of the 36 light projecting optical fibers 12 conform to each other. Specifically, the 36 light receiving optical fibers 22 are bundled in one piece, for example, such that the centers of the 36 light receiving optical fibers 22 and the centers of the 36 light projecting optical fibers 12 can overlap each other.

The four light receiving marker optical fibers 25 are arranged, for example, at substantially four corners of the 36 light receiving optical fibers 22 bundled in one piece such that the two-fold symmetry is maintained.

Furthermore, the four light receiving marker optical fibers 25 are bundled in one piece, for example, such that the centers of the four light receiving marker optical fibers 25 and the centers of the four light projecting marker optical fibers 15 conform to each other. Specifically, the four light receiving marker optical fibers 25 are bundled in one piece, for example, such that the centers of the four light receiving marker optical fibers 25 and the centers of the four light projecting marker optical fibers 15 can overlap each other.

The 40 dummy fibers 26 are arranged, for example, between the light receiving optical fibers 22 or the light receiving marker optical fibers 25 and the light receiving-side two-dimensional array fixing portion 23.

With the configuration in which any light receiving optical fiber 22, light receiving marker optical fiber 25, or dummy fiber 26 is arranged in contact with six other fibers in this manner, the centers of the fibers can be stably fixed at the locations of the vertices of equilateral triangles, and thus the center positions of the fibers can be prevented from being displaced from their design positions.

Note that the number of dummy fibers 26 is not limited to 40, and any number is possible as long as at least one layer of the dummy fibers 26 can be arranged between the light receiving optical fibers 22 or the light receiving marker optical fibers 25 and the light receiving-side two-dimensional array fixing portion 23.

Although a case was described in which the cross-sections of the light receiving optical fibers 22, the light receiving marker optical fibers 25, and the dummy fibers 26 are in the shape of circles, even in a case where the cross-sections of the fibers are in the shape of hexagons or the like, the fibers are arranged closer to each other than in a state where they are arranged in contact with each other in a square lattice, in the cross-section Sr.

The input ends of the cores 22a of the light receiving optical fibers 22 are arranged, for example, at positions that are respectively conjugate with the real images RIp shown in FIG. 4. With the configuration in which the input ends are arranged in this manner, the light receiving optical fibers 22 can suitably receive light respectively from the real images RIp.

Again referring to FIG. 1, the light receiving optical fibers 22 have a function of guiding the received light to the spectroscope 1. More specifically, the light receiving optical fibers 22 cause, for example, the receiving beam group received at their input ends to be converted into a plurality of one-dimensionally arranged beams (hereinafter, also referred to as a one-dimensional beam group) and to be incident on the spectroscope 1.

More specifically, for example, the light receiving-side one-dimensional array fixing portion 21 one-dimensionally fixes the output ends of the light receiving optical fibers 22 whose input ends are two-dimensionally arranged in the light receiving-side two-dimensional array fixing portion 23.

The spectroscope 1 includes a slit 1a and a diffraction grating 1b. The opening portion of the slit 1a is arranged, for example, so as to face the one-dimensional beam group and to be along a direction that is parallel to the arrangement direction of the one-dimensional beam group.

The plurality of beams contained in the one-dimensional beam group that have passed through the slit 1a are, for example, diffracted by the diffraction grating 1b into a direction that is orthogonal to the arrangement direction, and are irradiated onto the two-dimensional detector 2.

The two-dimensional detector 2 measures, for example, intensity at each wavelength, that is, a spectrum, for each beam contained in the one-dimensional beam group diffracted by the diffraction grating 1b. That is to say, for example, for the respective positions of the real images RIp shown in FIG. 4, the two-dimensional detector 2 measures spectra of the sample 61 irradiated with light that has passed through the corresponding light projecting optical fibers 12.

For example, in the configuration in which a light source that emits light having a single color such as a laser is used as the measurement light source 11, the microspectroscope 101 can be used as a confocal Raman spectroscopic microscope that can simultaneously measure Raman spectra at multiple points, or a confocal spectroscopic microscope that can simultaneously measure fluorescence spectra at multiple points.

Furthermore, for example, in the configuration in which a light source that emits light having a wide bandwidth such as a white light source is used as the measurement light source 11, the microspectroscope 101 can be used as a confocal spectral reflection microscope that can simultaneously measure spectral reflection spectra at multiple points.

Furthermore, for example, the confocal optical system 5 causes each of marker beams from the light projecting marker optical fibers 15 and marker beams from the light receiving marker optical fibers 25 to be condensed and irradiated onto the sample 61.

More specifically, the collimating lens 37 converts, for example, light spread apart from the output ends of the light projecting marker optical fibers 15, into a light projecting marker beam group consisting of substantially parallel beams.

Among wavelength components of light contained in the light projecting marker beam group from the collimating lens 37, the band-pass filter 38 attenuates, for example, wavelength components other than those at peaks in spectra of the laser light of the measurement light source 11.

The light projecting marker beam group transmitted through the band-pass filter 38 is, for example, reflected by the dichroic mirror 33 and the scanning mirror 34, and is incident on the object lens 36.

The object lens 36 condenses, for example, each of a plurality of beams contained in the light projecting marker beam group reflected by the scanning mirror 34, on the sample 61.

Furthermore, the condensing lens 31 converts, for example, light spread apart from the output ends of the light receiving marker optical fibers 25, into a light receiving marker beam group consisting of substantially parallel beams.

For example, wavelength components of light contained in the light receiving marker beam group from the condensing lens 31 are transmitted through the band-stop filter 32.

The light receiving marker beam group transmitted through the band-stop filter 32 is, for example, reflected by the scanning mirror 34, and is incident on the object lens 36.

The object lens 36 condenses, for example, each of a plurality of beams contained in the light receiving marker beam group reflected by the scanning mirror 34, on the sample 61.

Again referring to FIG. 4, the real images RIpm are, for example, real images of the output ends of the cores 15a of the four light projecting marker optical fibers 15, generated by causing each of beams from the output ends of the cores 15a to be condensed on the sample 61 by the confocal optical system 5.

Furthermore, the real images RIrm are, for example, real images of the output ends of the cores 25a of the four light receiving marker optical fibers 25, generated by causing each of beams from the output ends of the cores 25a to be condensed on the sample 61 by the confocal optical system 5.

The XYZ stage 62 can move, for example, in a direction that is perpendicular to the optical axis of the object lens 36 (hereinafter, also referred to as a lateral direction) and in a direction that is parallel to the optical axis (hereinafter, also referred to as a vertical direction). The sample 61 is, for example, placed on the XYZ stage 62, and is scanned in the lateral direction by moving the XYZ stage 62 in the lateral direction.

Furthermore, the scanning mirror 34 can rotate about rotational axes, for example, consisting of two axes that extend through the center of the mirror, that are contained on the mirror face, and that are orthogonal to each other. The positions at which beams contained in the projecting beam group are condensed on the sample 61 are scanned in the lateral direction, for example, by changing the reflection direction of the beams by rotating the scanning mirror 34 about the rotational axes consisting of the two axes.

For example, when observing the sample 61 in a reflection mode, the reflection illuminator 53 irradiates light onto the sample 61 from the object lens 36 side. More specifically, the movable half mirror 35 reflects, for example, beams emitted from the reflection illuminator 53 and collimated by the collimating lens 54, thereby guiding the beams via the object lens 36 to irradiate the sample 61.

Furthermore, for example, when observing the sample 61 in a transmission mode, the transmission illuminator 63 irradiates light onto the sample 61 from the side that is farther from the object lens 36 than the sample 61 is.

The observation optical system 4 condenses, for example, each of beams from the condensing points on the sample 61, on the observation camera 51.

More specifically, the object lens 36 in the observation optical system 4 collimates, for example, light spread apart from the sample 61. The movable half mirror 35 and the half mirror 55 reflect, for example, light collimated by the object lens 36.

The imaging lens 52 condenses, for example, light reflected by the half mirror 55, on the observation camera 51.

For example, the observation camera 51 generates an image containing the real images RIp, RIrm, and RIpm on the sample 61 based on the light from the sample 61 condensed by the observation optical system 4.

For example, the measurer can see positions in the lateral direction and the vertical direction of the real images RIp, RIrm, and RIpm on the sample 61 based on the image generated by the observation camera 51. The measurer adjusts, for example, the positions in the lateral direction of the real images RIp, RIrm, and RIpm on the sample 61, as necessary, by laterally moving the XYZ stage 62 or rotating the scanning mirror 34.

Furthermore, the measurer adjusts, for example, the positions in the vertical direction of the real images RIp, RIrm, and RIpm on the sample 61, as necessary, by vertically moving the XYZ stage 62. Note that the measurer may perform the adjustment by vertically moving the object lens 36 instead of vertically moving the XYZ stage 62.

Furthermore, the measurer can see, for example, a positional relationship between the real images RIpm and RIrm on the sample 61 based on the image.

In this case, a marker positional relationship, which is a positional relationship between the centers of the real images RIpm and the centers of the real images RIrm, corresponds to, for example, a relationship between the center positions of the input ends of the cores 22a of the light receiving optical fibers 22 and the condensing positions of light from the centers of the real images RIp on the input ends.

For example, if the centers of the real images RIpm and the centers of the corresponding real images RIrm match each other as shown in FIG. 4, light from the centers of the corresponding real images RIp is condensed on the centers of the input ends of the cores 22a of the light receiving optical fibers 22. That is to say, the cores 22a of the light receiving optical fibers 22 can suitably receive light respectively from the real images RIp.

The measurer sees, for example, whether or not the input ends of the cores 22a of the light receiving optical fibers 22 suitably receive light respectively from the real images RIp, based on the marker positional relationship.

If the centers of the real images RIpm and the centers of the corresponding real images RIrm are displaced from each other, for example, the measurer adjusts the positions and the orientations of the optical elements in the confocal optical system 5, the light projecting-side two-dimensional array fixing portion 13, and the light receiving-side two-dimensional array fixing portion 23 such that the centers of the real images RIpm and the centers of the corresponding real images RIrm match each other, thereby enabling the input ends of the cores 22a of the light receiving optical fibers 22 to suitably receive light respectively from the real images RIp.

For example, the light projecting marker light source 14 and the light receiving marker light source 24 output light having mutually different colors. Specifically, for example, if the measurement light source 11 is a laser light source that emits green light, the light projecting marker light source 14 and the light receiving marker light source 24 respectively output green light and red light.

Accordingly, the color of the real images RIpm and the color of the real images RIrm can be respectively set to green and red, so that the measurer can more reliably distinguish the real images RIpm from the real images RIrm. Furthermore, the color of each portion where the region of a real image RIpm and the region of a real image RIrm overlap each other becomes yellow, which is a color obtained by additive mixture of green and red, and thus, based on a positional relationship between the red real image RIrm and the yellow overlap portion, the measurer can clearly see displacement between the center of the real image RIpm and the center of the corresponding real image RIrm.

When performing measurement using the spectroscope 1, for example, the movable half mirror 35 moves to a position withdrawn from the optical path of the projecting beam group.

Furthermore, for example, if LEDs are used as the light projecting marker light source 14 and the light receiving marker light source 24, a peak emission wavelength λpp of the light projecting marker light source 14 and a peak emission wavelength λpr of the light receiving marker light source 24 may be set as in the following example.

That is to say, for example, if an oscillation wavelength λL of the laser light of the measurement light source 11 is 488 nm (nanometer) in blue, the peak emission wavelengths λpp and λpr may be set respectively to 490 nm in blue and 530 nm in green, in consideration of the attenuation characteristics of the band-pass filter 38 and the band-stop filter 32.

Furthermore, for example, if the oscillation wavelength λL is 532 nm in green, the peak emission wavelengths λpp and λpr may be set respectively to 530 nm in green and 625 nm in red, in consideration of the attenuation characteristics of the filters in a similar manner.

Furthermore, for example, if the oscillation wavelength λL is 635 nm in red, the peak emission wavelengths λpp and λpr may be set respectively to 625 nm in red and 780 nm in red, in consideration of the attenuation characteristics of the filters in a similar manner.

Furthermore, for example, if the oscillation wavelength λL is 785 nm in red, the peak emission wavelengths λpp and λpr may be set respectively to 780 nm in red and 830 nm in a near infrared region, in consideration of the attenuation characteristics of the filters in a similar manner. For example, if a CCD (charge coupled device) is used as an image sensor in the observation camera 51, since a CCD is sensitive to visible light as well as near infrared light (e.g., at 830 nm) that is barely visible to the naked eye, the measurer can view the real images RIpm and RIrm from the image captured by the observation camera 51.

Modified Example of the Light Projecting Portion 6

Figure 6:
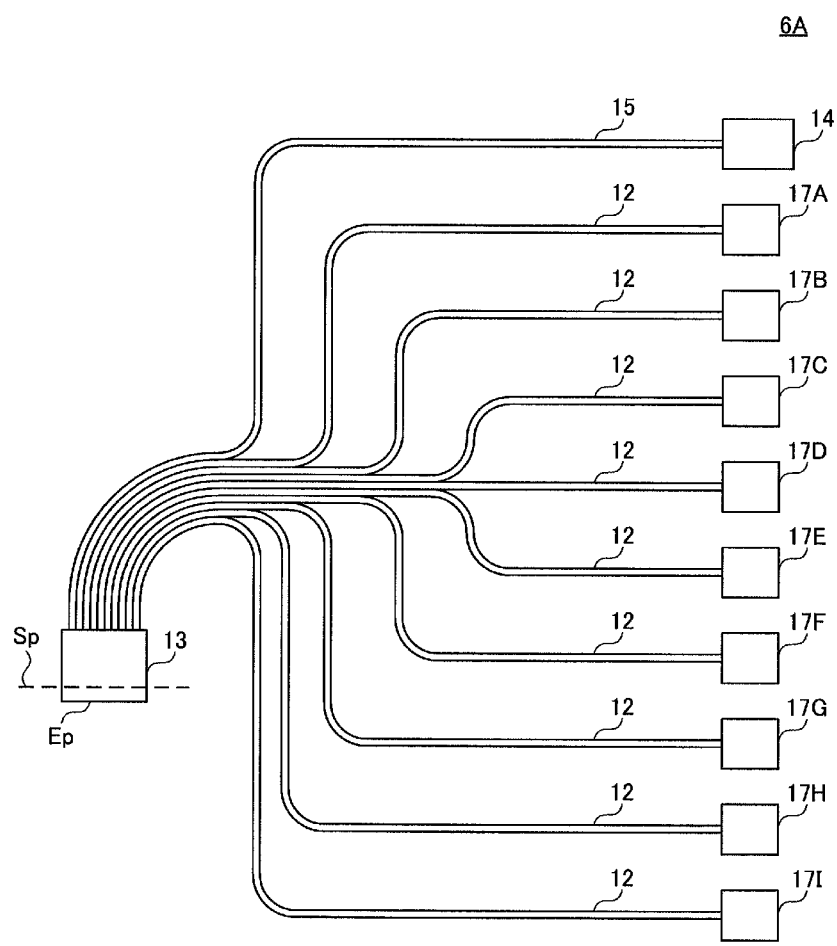
FIG. 6 is a view showing the configuration of a modified example of a light projecting portion in the microspectroscope according to the first embodiment of the present invention.

FIG. 6 is a view showing the configuration of a modified example of a light projecting portion in the microspectroscope according to the first embodiment of the present invention.

Referring to FIG. 6, a light projecting portion 6A is different from the light projecting portion 6 shown in FIG. 1, in that it includes a plurality of measurement light sources 17 instead of the measurement light source 11.

In this example, the light projecting portion 6A includes, for example, measurement light sources 17A to 17I. Hereinafter, each of the measurement light sources 17A to 17I also may be referred to as a measurement light source 17.

Each measurement light source 17 is, for example, a light source that generates light, and is specifically a laser that outputs light having a single color. The measurement light source 17 may be an LED that outputs light having a wide bandwidth, an incandescent electric lamp, or the like.

The plurality of light projecting optical fibers 12 receive, for example, light from the plurality of measurement light sources 17. Each measurement light source 17 irradiates light, for example, onto one or a plurality of corresponding light projecting optical fibers 12, which are part of the plurality of light projecting optical fibers 12.

Specifically, the 36 light projecting optical fibers 12 receive, for example, light from nine measurement light sources 17. Each measurement light source 17 irradiates light, for example, onto four corresponding light projecting optical fibers 12, which are part of the 36 light projecting optical fibers 12.

The configuration of each measurement light source 17 is not limited to that in which it irradiates light onto four corresponding light projecting optical fibers 12, which are part of the 36 light projecting optical fibers 12, and a configuration is also possible in which the measurement light source 17 irradiates light onto three or less or five or more corresponding light projecting optical fibers 12.

The optical paths of the light from the measurement light sources 17 are regulated, for example, such that light that is received by each light projecting optical fiber 12 is light from one corresponding measurement light source 17. In other words, for example, the optical paths between the measurement light sources 17 and the light projecting optical fibers 12 are regulated such that light from one measurement light source 17 is irradiated onto one or a plurality of corresponding light projecting optical fibers 12.

Specifically, for example, the measurement light sources 17 are covered by casings that can block light. Furthermore, for example, the light projecting optical fibers 12 are optically coupled to the measurement light sources 17 in the casings.

Compared with the light projecting portion 6 in which one measurement light source 11 is used for 36 light projecting optical fibers 12, the light projecting portion 6A is such that nine measurement light sources 17 are used for 36 light projecting optical fibers 12, that is, one measurement light source 17 is used for four light projecting optical fibers 12 in this manner, and thus the intensity of laser light received by each light projecting optical fiber 12 can be increased.

Accordingly, the intensity of light irradiated onto the sample 61 can be increased, and thus, for example, a Raman spectrum or a fluorescence spectrum can be suitably measured.

Furthermore, the magnitude of a Raman shift in a Raman spectrum corresponds to a difference between the frequency of scattered light and the frequency of excitation light, and thus it is preferable that the sample 61 is irradiated with light having a single color. On the other hand, in the above-described configuration in which each light projecting optical fiber 12 can be prevented from receiving light from a plurality of measurement light sources 17 in the light projecting portion 6A, and the confocal optical system 5 is used, a Raman spectrum using light from a single measurement light source 17 as excitation light can be measured at each of the positions of the real images RIp on the sample 61. Accordingly, even in the case where laser oscillation frequencies vary between the measurement light sources 17, the magnitude of the Raman shift can be accurately obtained at each of the positions of the real images Rip based on the laser oscillation frequency of the corresponding measurement light source 17.

Measuring Method

Figure 7:
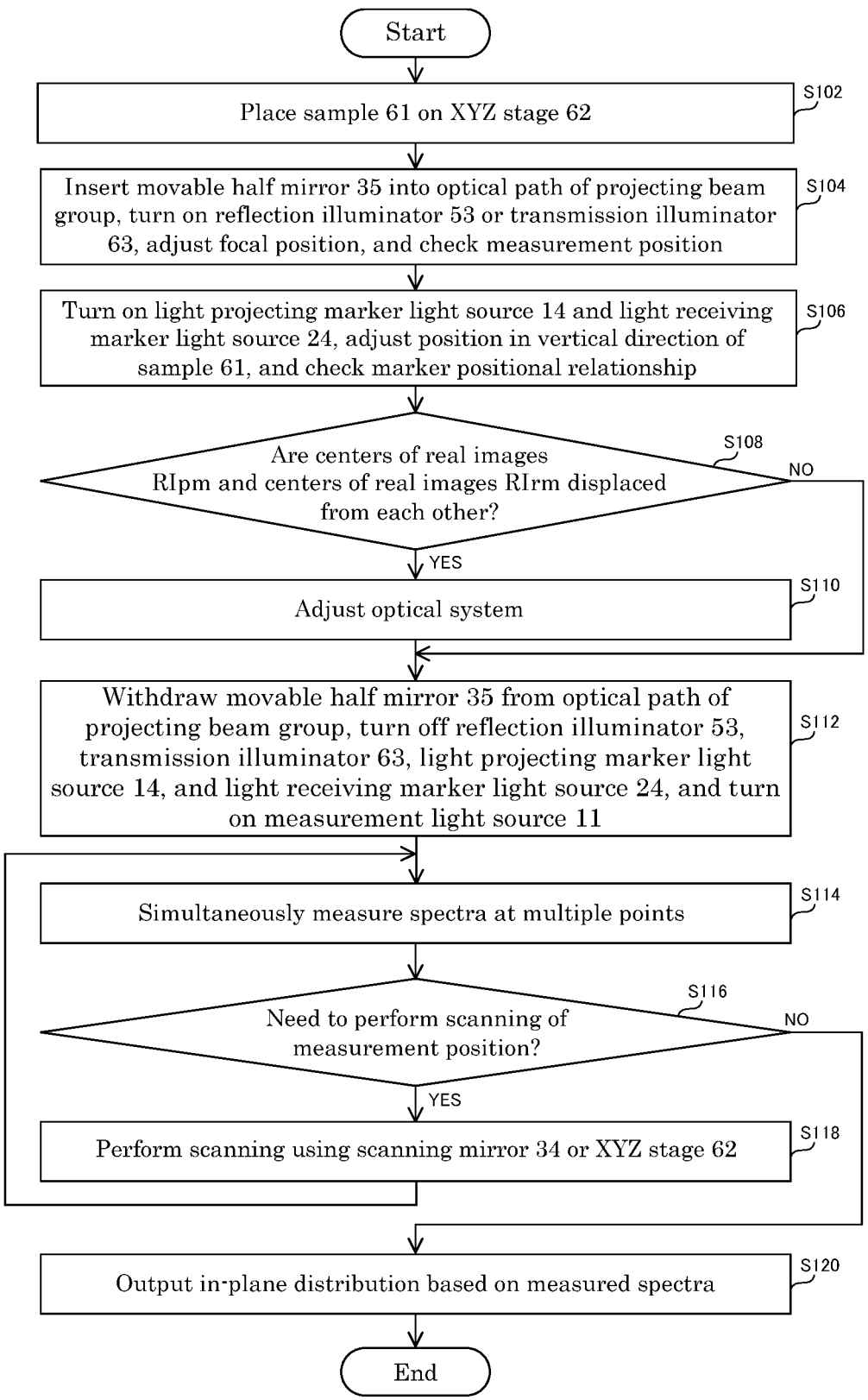
FIG. 7 is a flowchart defining an example of the procedure of a measuring method using the microspectroscope according to the first embodiment of the present invention.

FIG. 7 is a flowchart defining an example of the procedure of a measuring method using the microspectroscope according to the first embodiment of the present invention.

Referring to FIG. 7, first, the measurer places the sample 61 on the XYZ stage 62 (step S102).

Next, the measurer inserts the movable half mirror 35 into the optical path of the projecting beam group, turns on the reflection illuminator 53 or the transmission illuminator 63, adjusts the focal position, and checks the measurement position (step S104).

Next, the measurer turns on the light projecting marker light source 14 and the light receiving marker light source 24, adjusts the positions in the vertical direction of the real images RIrm and RIpm on the sample 61, and checks the positional relationship between the centers of the real images RIpm and the centers of the real images RIrm, that is, the marker positional relationship (step S106).

Next, if the centers of the real images RIpm and the centers of the real images RIrm are displaced from each other (YES in step S108), in order to solve the displacement, the measurer adjusts the positions and the orientations of the optical elements in the confocal optical system 5, the light projecting-side two-dimensional array fixing portion 13, and the light receiving-side two-dimensional array fixing portion 23 (step S110).

Next, if the measurer sees that the centers of the real images RIpm and the centers of the real images RIrm are not displaced from each other (NO in step S108) or the optical system has been adjusted (step S110), the measurer withdraws the movable half mirror 35 from the optical path of the projecting beam group, turns off the reflection illuminator 53, the transmission illuminator 63, the light projecting marker light source 14, and the light receiving marker light source 24, and turns on the measurement light source 11 (step S112).

Next, the measurer simultaneously measures spectra at multiple points (step S114).

Next, if scanning of the measurement position is necessary (YES in step S116), the measurer rotates the scanning mirror 34 or laterally moves the XYZ stage 62 (step S118).

Next, the measurer simultaneously measures spectra at multiple points after the scanning (step S114).

On the other hand, if scanning of the measurement position is not necessary or is ended (NO in step S116), the measurer calculates the spectral characteristic amount at each position based on the measured spectrum, and generates and outputs in-plane distribution of the calculated characteristic amount (step S120). Note that the spectral characteristic amount is, for example, the magnitude of a Raman shift, the intensity of a peak, the transmittance, the reflectance, the chromaticity, or the like.

Note that, in this specification, "simultaneously measuring spectra at multiple points" may refer to performing parallel measurement of spectra at multiple points.

Although the configuration was described in which the light projecting optical fibers 12 and the light receiving optical fibers 22 according to the first embodiment of the present invention are individually two-dimensionally arranged, there is no limitation to this. The light projecting optical fibers 12 and the light receiving optical fibers 22 may be individually one-dimensionally arranged.

Although the configuration was described in which the microspectroscope according to the first embodiment of the present invention includes the plurality of light projecting marker optical fibers 15, there is no limitation to this. The microspectroscope 101 may be configured so as to include one light projecting marker optical fiber 15.

Although the configuration was described in which the microspectroscope according to the first embodiment of the present invention includes the plurality of light receiving marker optical fibers 25, there is no limitation to this. The microspectroscope 101 may be configured so as to include one light receiving marker optical fiber 25.

For example, in the configuration in which the microspectroscope 101 includes one light projecting marker optical fiber 15 and one light receiving marker optical fiber 25, if the core 15a of the light projecting marker optical fiber 15 and the core 25a of the light receiving marker optical fibers 25 have a shape such as a quadrangle whose angles can be identified, a relationship between the center positions of the input ends of the cores 22a of the light receiving optical fibers 22 and the condensing positions of light from the centers of the real images RIp on the input ends can be seen. Accordingly, the optical system can be easily adjusted.

Furthermore, for example, the microspectroscope 101 is configured so as to include two light projecting marker optical fibers 15, the two light projecting marker optical fibers 15 may be arranged respectively at diagonal positions of the substantially four corners of the 36 light projecting optical fibers 12 bundled in one piece, in the light projecting end face Ep.

Furthermore, for example, if the microspectroscope 101 is configured so as to include two light receiving marker optical fibers 25, the two light receiving marker optical fibers 25 may be arranged respectively at diagonal positions of the substantially four corners of the 36 light receiving optical fibers 22 bundled in one piece, in the light receiving end face Er.

Although the configuration was described in which the microspectroscope according to the first embodiment of the present invention includes the light projecting optical fibers 12, the light projecting marker optical fibers 15, and the dummy fibers 16, there is no limitation to this. The microspectroscope 101 may be configured so as not to include at least either the light projecting marker optical fibers 15 or the dummy fibers 16.

Although the configuration was described in which the microspectroscope according to the first embodiment of the present invention includes the light receiving optical fibers 22, the light receiving marker optical fibers 25, and the dummy fibers 26, there is no limitation to this. The microspectroscope 101 may be configured so as not to include at least either the light receiving marker optical fibers 25 or the dummy fibers 26.

For example, in the configuration in which the microspectroscope 101 does not include the light receiving marker optical fibers 25, if the light receiving optical fibers 22 are detached from the spectroscope 1 and light is irradiated onto the output ends of the light receiving optical fibers 22, or light is irradiated from the diffraction grating 1b side of the slit 1a toward the output ends of the light receiving optical fibers 22, real images RIr of the cores 22a of the 36 light receiving optical fibers 22 are generated on the sample 61. Furthermore, if the measurement light source 11 is turned on, the real images RIp are generated on the sample 61. When the real images RIr and Rip are used, a relationship between the center positions of the input ends of the cores 22a of the light receiving optical fibers 22 and the condensing positions of light from the centers of the real images RIp on the input ends can be seen. Accordingly, the optical system can be adjusted.

Furthermore, the microspectroscope according to the first embodiment of the present invention may be configured so as not to include the light projecting marker light source 14. In this case, for example, the light projecting marker optical fibers 15 receive light from the measurement light source 11, on the input end side of the light projecting optical fibers 12.

Furthermore, the microspectroscope according to the first embodiment of the present invention may be configured so as not to include the light receiving marker light source 24.

In this case, for example, the light receiving marker optical fibers 25 receive light from the measurement light source 11, on the output end side of the light receiving optical fibers 22.

Although the configuration was described in which the microspectroscope according to the first embodiment of the present invention has the light projecting optical fibers 12 and the light receiving optical fibers 22 both of which are arranged closer to each other than in a state in which the optical fibers are arranged in contact with each other in a square lattice, in the cross-section Sp or Sr cut along a plane that is orthogonal to the extending direction of the optical fibers, there is no limitation to this. It is also possible to adopt a configuration in which either the light projecting optical fibers 12 or the light receiving optical fibers 22 are arranged closer to each other than in a state in which the optical fibers are arranged in contact with each other in a square lattice, in the corresponding cross-section Sp or Sr.

Although the configuration was described in which the microspectroscope according to the first embodiment of the present invention is such that the outer diameter Rr of the core 22a of each light receiving optical fiber 22 is larger than the outer diameter Rp of the core 12a of each light projecting optical fiber 12, there is no limitation to this. The outer diameter Rr may be the same as the outer diameter Rp, or may be smaller than the outer diameter Rp.

Incidentally, there is a demand for techniques for providing devices, the techniques being superior to those described in the above-described Patent Documents.

More specifically, according to the multifocal confocal microscopes of Patent Documents 1 and 2, the confocal optical system has to be provided with a pinhole array, resulting in problems in which the optical system has a complex configuration and in which adjustment of the optical system is difficult.

On the other hand, according to the microspectroscope of the first embodiment of the present invention, the plurality of light projecting optical fibers 12 receive light from the measurement light source 11. The plurality of light receiving optical fibers 22 guide the received light to the spectroscope 1. The confocal optical system 5 causes each of a plurality of beams from the plurality of light projecting optical fibers 12 to be condensed and irradiated onto the sample 61, and forms images of a plurality of beams from a plurality of condensing points on the sample 61, respectively on the plurality of light receiving optical fibers 22.

In this manner, a multifocal and confocal configuration is realized by paying attention to the use of the plurality of light projecting optical fibers 12 and the plurality of light receiving optical fibers 22, so that light from a plurality of positions on the sample 61 can be separated with a simple and easily adjustable configuration in which the number of optical elements is small and no pinhole array is provided in the optical system, for example, contrary to the multifocal confocal microscopes according to Patent Documents 1 and 2. Accordingly, it is possible to provide a superior microspectroscope.

Furthermore, according to the microspectroscope of the first embodiment of the present invention, the plurality of light projecting optical fibers 12 and the plurality of light receiving optical fibers 22 are individually two-dimensionally arranged. Furthermore, at least either the plurality of light projecting optical fibers 12 or the plurality of light receiving optical fibers 22 are arranged closer to each other than in a state in which the optical fibers are arranged in contact with each other in a square lattice, in the cross-section Sp or Sr cut along a plane that is orthogonal to the extending direction of the optical fibers.

With this configuration, the number of optical fibers per unit area in the cross-section Sp or Sr can be increased, and thus the area of light irradiated by the measurement light source 11 onto the light projecting optical fibers 12 can be made smaller. Accordingly, the amount of light received by one light projecting optical fiber 12 from the measurement light source 11 can be increased, and thus the usage efficiency of light can be improved. Furthermore, the occupancy of the device by the optical fibers can be made smaller.

Furthermore, according to the microspectroscope of the first embodiment of the present invention, the light projecting marker optical fibers 15 are fixed along the plurality of light projecting optical fibers 12, and receive light from the light projecting marker light source 14, on the input end side of the light projecting optical fibers 12. The light receiving marker optical fibers 25 are fixed along the plurality of light receiving optical fibers 22, and receive light from the light receiving marker light source 24, on the output end side of the light receiving optical fibers 22. The confocal optical system 5 causes each of marker beams from the light projecting marker optical fibers 15 and marker beams from the light receiving marker optical fibers 25 to be condensed and irradiated onto the sample 61.

With this configuration, based on a relationship between the condensing positions of marker beams from the light projecting marker optical fibers 15 and the condensing positions of marker beams from the light receiving marker optical fibers 25, a relationship between the condensing positions of beams from the condensing points on the sample 61 and the positions of the light receiving optical fibers 22 can be seen, and whether or not the state of the optical system is suitable can be easily determined. Accordingly, for example, when the state of the optical system is not suitable, the arrangement of the optical elements in the optical system can be altered so that the state of the optical system can be kept suitable.

Furthermore, according to the microspectroscope of the first embodiment of the present invention, the light projecting marker light source 14 and the light receiving marker light source 24 output light having mutually different colors.

With this configuration, marker beams having mutually different colors from the light projecting marker optical fibers 15 and the light receiving marker optical fibers 25 can be irradiated onto the sample 61, and thus whether or not the state of the optical system is suitable can be more easily determined.

Furthermore, the microspectroscope according to the first embodiment of the present invention includes the plurality of measurement light sources 17. The plurality of light projecting optical fibers 12 receive light from the plurality of measurement light sources 17. Each measurement light source 17 irradiates light onto one or a plurality of corresponding light projecting optical fibers 12, which are part of the plurality of light projecting optical fibers 12. The optical paths of the light from the measurement light sources 17 are regulated such that light that is received by each light projecting optical fiber 12 is light from one corresponding measurement light source 17.

With this configuration, the number of light projecting optical fibers 12 that are targets of irradiation by one measurement light source 17 can be reduced, and thus the intensity of light received by each light projecting optical fiber 12 from the measurement light source 17 can be increased. Accordingly, light from the condensing points on the sample 61 can be more suitably separated. Furthermore, one light projecting optical fiber 12 can be prevented from receiving light from a plurality of measurement light sources 17, and thus each condensing point on the sample 61 can be irradiated with light from a single measurement light source 17. Accordingly, spectral results of light from the condensing points on the sample 61 can be prevented from reflecting variations between the measurement light sources 17 in spectral characteristics of light irradiated from the measurement light sources 17.

Furthermore, according to the microspectroscope of the first embodiment of the present invention, the outer diameter Rr of the core 22a of each light receiving optical fiber 22 is larger than the outer diameter Rp of the core 12a of each light projecting optical fiber 12.

With this configuration, the margin for displacement between the condensing positions of beams from the condensing points on the sample 61 and the center positions of the cores 22a of the light receiving optical fibers 22 can be more reliably ensured.

Next, another embodiment of the present invention will be described with reference to the drawings. Note that the same or corresponding constituent elements in the drawings are denoted by the same reference numerals, and a description thereof will not be repeated.

Second Embodiment

This embodiment relates to a microspectroscope that is different from the microspectroscope according to the first embodiment, in that it uses no optical fibers on the light projecting side. The microspectroscope is similar to that according to the first embodiment, except for the aspects that will be described below.

Figure 8:
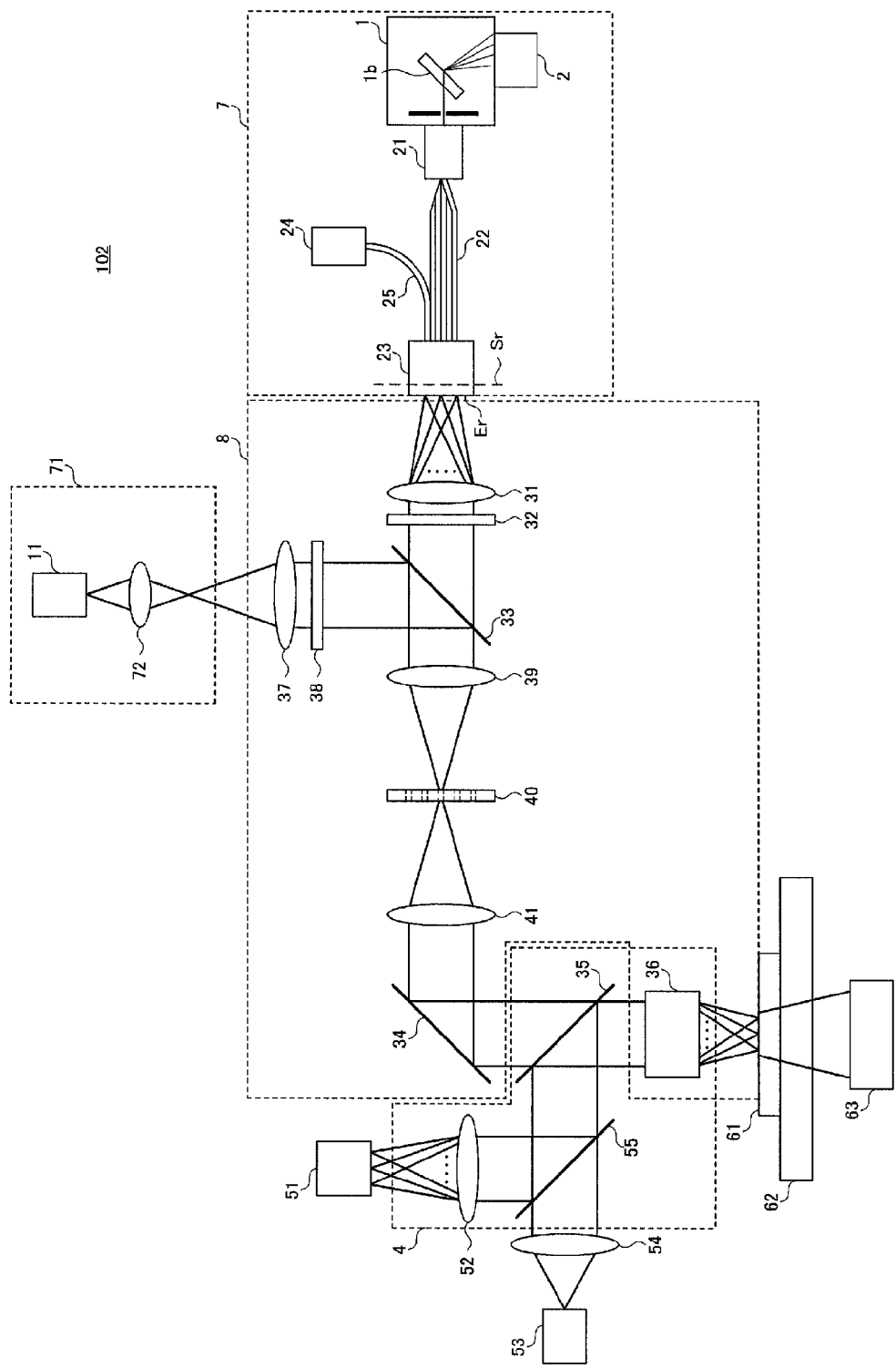
FIG. 8 is a view showing the configuration of a microspectroscope according to a second embodiment of the present invention.

FIG. 8 is a view showing the configuration of the microspectroscope according to the second embodiment of the present invention.

Referring to FIG. 8, a microspectroscope 102 includes the observation optical system 4, the light receiving portion 7, a confocal optical system 8, a light projecting portion 71, the observation camera 51, the reflection illuminator 53, the collimating lens 54, the XYZ stage 62, and the transmission illuminator 63.

The functions of the observation optical system 4, the light receiving portion 7, the observation camera 51, the reflection illuminator 53, the collimating lens 54, the XYZ stage 62, and the transmission illuminator 63 in the microspectroscope 102 are respectively similar to those of the observation optical system 4, the light receiving portion 7, the observation camera 51, the reflection illuminator 53, the collimating lens 54, the XYZ stage 62, and the transmission illuminator 63 in the microspectroscope 101 shown in FIG. 1.

The light projecting portion 71 includes the measurement light source 11 and a lens 72. The function of the measurement light source 11 in the light projecting portion 71 is similar to that of the measurement light source 11 in the light projecting portion 6 shown in FIG. 1.

The confocal optical system 8 further includes a first lens 39, a pinhole plate 40, and a second lens 41, in addition to the constituent elements of the confocal optical system 5 shown in FIG. 1. The functions of the condensing lens 31, the band-stop filter 32, the dichroic mirror 33, the scanning mirror 34, the object lens 36, the collimating lens 37, and the band-pass filter 38 in the confocal optical system 8 are respectively similar to those of the condensing lens 31, the band-stop filter 32, the dichroic mirror 33, the scanning mirror 34, the object lens 36, the collimating lens 37, and the band-pass filter 38 in the confocal optical system 5 shown in FIG. 1.

The measurement light source 11 in the light projecting portion 71 irradiates light, for example, via the lens 72 onto the collimating lens 37. In this example, the lens 72 condenses, for example, the light spread apart from the measurement light source 11 such that a beam waist is formed between the lens 72 and the collimating lens 37.

The confocal optical system 8 has a function of causing each of a plurality of beams from the measurement light source 11 to be condensed and irradiated onto the sample 61, and forming images of a plurality of beams from a plurality of condensing points on the sample 61, respectively on the plurality of light receiving optical fibers 22.

More specifically, the collimating lens 37 converts, for example, light received from the measurement light source 11 via the lens 72, into projecting beams consisting of substantially parallel beams.

Among wavelength components of laser light contained in the projecting beams from the collimating lens 37, the band-pass filter 38 attenuates, for example, wavelength components other than those at peaks in spectra of the laser light.

The projecting beams transmitted through the band-pass filter 38 are, for example, reflected by the dichroic mirror 33, and are incident on the first lens 39.

The first lens 39 condenses, for example, each of the projecting beams reflected by the dichroic mirror 33, on the pinhole plate 40.

Figure 9:
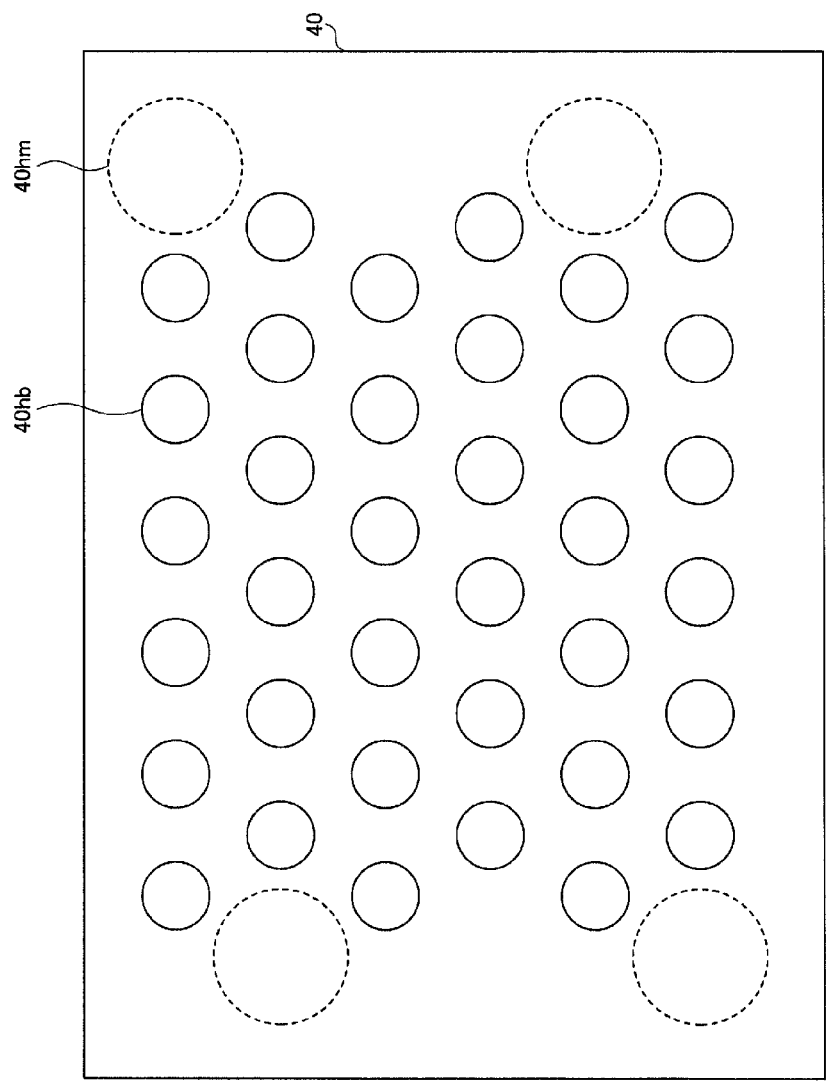
FIG. 9 is a plan view of a main surface of a pinhole plate in the microspectroscope according to the second embodiment of the present invention.

FIG. 9 is a plan view of a main surface of a pinhole plate in the microspectroscope according to the second embodiment of the present invention.

In FIG. 9, projecting light generating holes 40hb and marker light generating holes 40hm are respectively represented by solid lines and broken lines.

Referring to FIG. 9, the pinhole plate 40 is provided with, for example, 36 projecting light generating holes 40hb and four marker light generating holes 40hm. Each of the marker light generating holes 40hm has a diameter that is, for example, larger than the diameter of each of the projecting light generating holes 40hb.

More specifically, the 36 projecting light generating holes 40hb are respectively arranged, for example, at positions that conform to the cores 12a of the light projecting optical fibers 12 shown in FIG. 2.

Specifically, the projecting light generating holes 40hb are arranged, for example, so as to be two-dimensionally arranged in an equilateral triangle lattice, in a plan view in a direction that is along the propagation direction of projecting beams. Furthermore, the projecting light generating holes 40hb are arranged, for example, so as to have two-fold symmetry, in the plan view.

More specifically, the 36 projecting light generating holes 40hb consist of for example, six layers each including six projecting light generating holes 40hb.

The four marker light generating holes 40hm are respectively arranged, for example, at positions that conform to the cores 15a of the light projecting marker optical fibers 15 shown in FIG. 2.

Specifically, the marker light generating holes 40hm are arranged, for example, at substantially four corners of the 36 arranged projecting light generating holes 40hb, in a plan view in a direction that is along the propagation direction of projecting beams.

The 36 projecting light generating holes 40hb generate, for example, 36 light sources from the projecting beams condensed by the first lens 39, at the pinhole plate 40 on one side thereof that is farther from the first lens 39 than the other side is.

In a similar manner, the four marker light generating holes 40*hm* generate, for example, four light sources from the projecting beams condensed by the first lens 39, at the pinhole plate 40 on one side thereof that is farther from the first lens 39 than the other side is.

The second lens 41 converts, for example, light spread apart from the light sources generated by the projecting light generating holes 40*hb*, into a projecting beam group consisting of substantially parallel beams, and converts light spread apart from the light sources generated by the marker light generating holes 40*hm*, into a light projecting marker beam group consisting of substantially parallel beams.

The scanning mirror 34 reflects, for example, the projecting beam group and the light projecting marker beam group from the second lens 41, toward the object lens 36.

The object lens 36 condenses, for example, each of a plurality of beams contained in the projecting beam group and the light projecting marker beam group reflected by the scanning mirror 34, on the sample 61.

Figure 10:
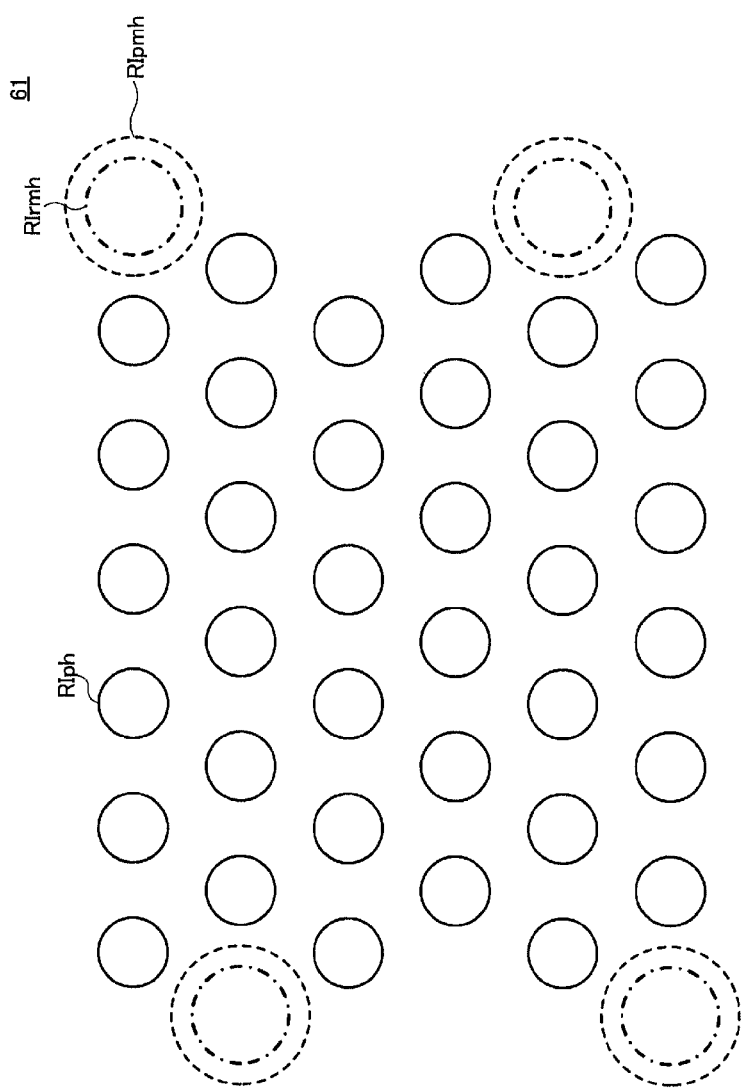
FIG. 10 is a view showing an example of real images formed on a sample in the microspectroscope according to the second embodiment of the present invention.

FIG. 10 is a view showing an example of real images formed on a sample in the microspectroscope according to the second embodiment of the present invention.

In FIG. 10, real images RIph, real images RIpmh, and real images RIrmh are respectively represented by solid lines, broken lines, and dashed dotted lines.

Referring to FIG. 10, the real images RIph are, for example, real images of the 36 projecting light generating holes 40*hb* of the pinhole plate 40, generated by causing each of beams from the projecting light generating holes 40*hb* to be condensed on the sample 61 by the confocal optical system 8.

The real images RIpmh are, for example, real images of the four marker light generating holes 40*hm* of the pinhole plate 40, generated by causing each of beams from the marker light generating holes 40*hm* to be condensed on the sample 61 by the confocal optical system 8.

Again referring to FIG. 8, the object lens 36 converts, for example, light spread apart from the real images RIph, into a receiving beam group consisting of substantially parallel beams.

The scanning mirror 34 reflects, for example, the receiving beam group converted by the object lens 36.

The second lens 41 condenses, for example, a plurality of beams contained in the receiving beam group reflected by the scanning mirror 34, respectively on the corresponding projecting light generating holes 40*hb* of the pinhole plate 40.

The first lens 39 collimates, for example, the receiving beam group that has passed through the projecting light generating holes 40*hb*.

Among wavelength components of light contained in the receiving beam group collimated by the first lens 39, the band-stop filter 32 attenuates, for example, wavelength components at peaks in spectra of the laser light of the measurement light source 11.

The condensing lens 31 condenses, for example, a plurality of beams contained in the receiving beam group transmitted through the band-stop filter 32, respectively on the cores 22*a* of the corresponding light receiving optical fibers 22.

Furthermore, the confocal optical system 8 causes each of a plurality of marker beams from the plurality of light receiving marker optical fibers 25 to be condensed and irradiated onto the sample 61.

More specifically, the condensing lens 31 converts, for example, light spread apart from the output ends of the light receiving marker optical fibers 25, into a light receiving marker beam group consisting of substantially parallel beams.

For example, wavelength components of light contained in the light receiving marker beam group from the condensing lens 31 are transmitted through the band-stop filter 32.

The first lens 39 condenses, for example, a plurality of beams contained in the light receiving marker beam group transmitted through the band-stop filter 32, respectively on the marker light generating holes 40*hm* of the pinhole plate 40 shown in FIG. 9. In this example, the light receiving marker beam through each marker light generating hole 40*hm* has a beam diameter that is, for example, smaller than the diameter of the marker light generating hole 40*hm*, and thus each beam contained in the light receiving marker beam group passes through the corresponding marker light generating hole 40*hm*.

The second lens 41 collimates, for example, the light receiving marker beam group that has passed through the marker light generating holes 40*hm*.

The scanning mirror 34 reflects, for example, the light receiving marker beam group collimated by the second lens 41, toward the object lens 36.

The object lens 36 condenses, for example, each of a plurality of beams contained in the light receiving marker beam group reflected by the scanning mirror 34, on the sample 61.

Again referring to FIG. 10, the real images RIrmh are, for example, real images of the output ends of the cores 25*a* of the four light receiving marker optical fibers 25, generated by causing each of beams that were emitted from the output ends of the cores 25*a* and have passed through the four marker light generating holes 40*hm* of the pinhole plate 40 to be condensed on the sample 61 by the confocal optical system 8.

With the above-described configuration in which the diameter of each of the marker light generating holes 40*hm* is larger than the diameter of each of the projecting light generating holes 40*hb*, the real images RIrmh free from defects resulting from the marker light generating holes 40*hm* can be formed on the sample 61. Accordingly, the measurer can more accurately see whether or not the input ends of the cores 22*a* of the light receiving optical fibers 22 suitably receive light respectively from the real images RIph, based on the marker positional relationship, which is a positional relationship between the centers of the real images RIpmh and the centers of the real images RIrmh.

As described above, according to the microspectroscope of the second embodiment of the present invention, the plurality of light receiving optical fibers 22 are two-dimensionally arranged, and guide the received light to the spectroscope 1. The confocal optical system 8 causes each of a plurality of beams from the measurement light source 11 to be condensed and irradiated onto the sample 61, and forms images of a plurality of beams from a plurality of condensing points on the sample 61, respectively on the plurality of light receiving optical fibers 22. The plurality of light receiving optical fibers 22 are two-dimensionally arranged, and are arranged closer to each other than in a state in which the optical fibers are arranged in contact with each other in a square lattice, in the cross-section Sr cut along a plane that is orthogonal to the extending direction of the optical fibers. The light receiving marker optical fibers 25 are fixed along the plurality of light receiving optical fibers 22, and receive light from the light receiving marker light source 24, on the output end side of the light receiving optical fibers 22. The confocal optical system 8 causes each of a plurality of marker beams from the plurality of light receiving marker optical fibers 25 to be condensed and irradiated onto the sample 61.

With this configuration, for example, based on a relationship between the condensing positions of a plurality of light projecting marker beams formed by light from the measurement light source 11 and the condensing positions of the marker beams from the light receiving marker optical fibers 25, a relationship between the condensing positions of beams from the condensing points on the sample 61 and the positions of the light receiving optical fibers 22 can be seen, and whether or not the state of the optical system is suitable can be easily determined, with a simple and easily adjustable configuration. Accordingly, for example, when the state of the optical system is not suitable, the arrangement of the optical elements in the optical system can be altered so that the state of the optical system can be kept suitable. Furthermore, the occupancy of the device by the light receiving optical fibers 22 can be made smaller. Accordingly, it is possible to provide a superior microspectroscope.

The other aspects of the configuration and the other operations are similar to those of the microspectroscope 101 according to the first embodiment, and thus a detailed description thereof will not be repeated.

Next, another embodiment of the present invention will be described with reference to the drawings. Note that the same or corresponding constituent elements in the drawings are denoted by the same reference numerals, and a description thereof will not be repeated.

Third Embodiment

This embodiment relates to a microspectroscope that is different from the microspectroscope according to the first embodiment, in that it uses no optical fibers on the light projecting side. The microspectroscope is similar to that according to the first embodiment, except for the aspects that will be described below.

Figure 11:
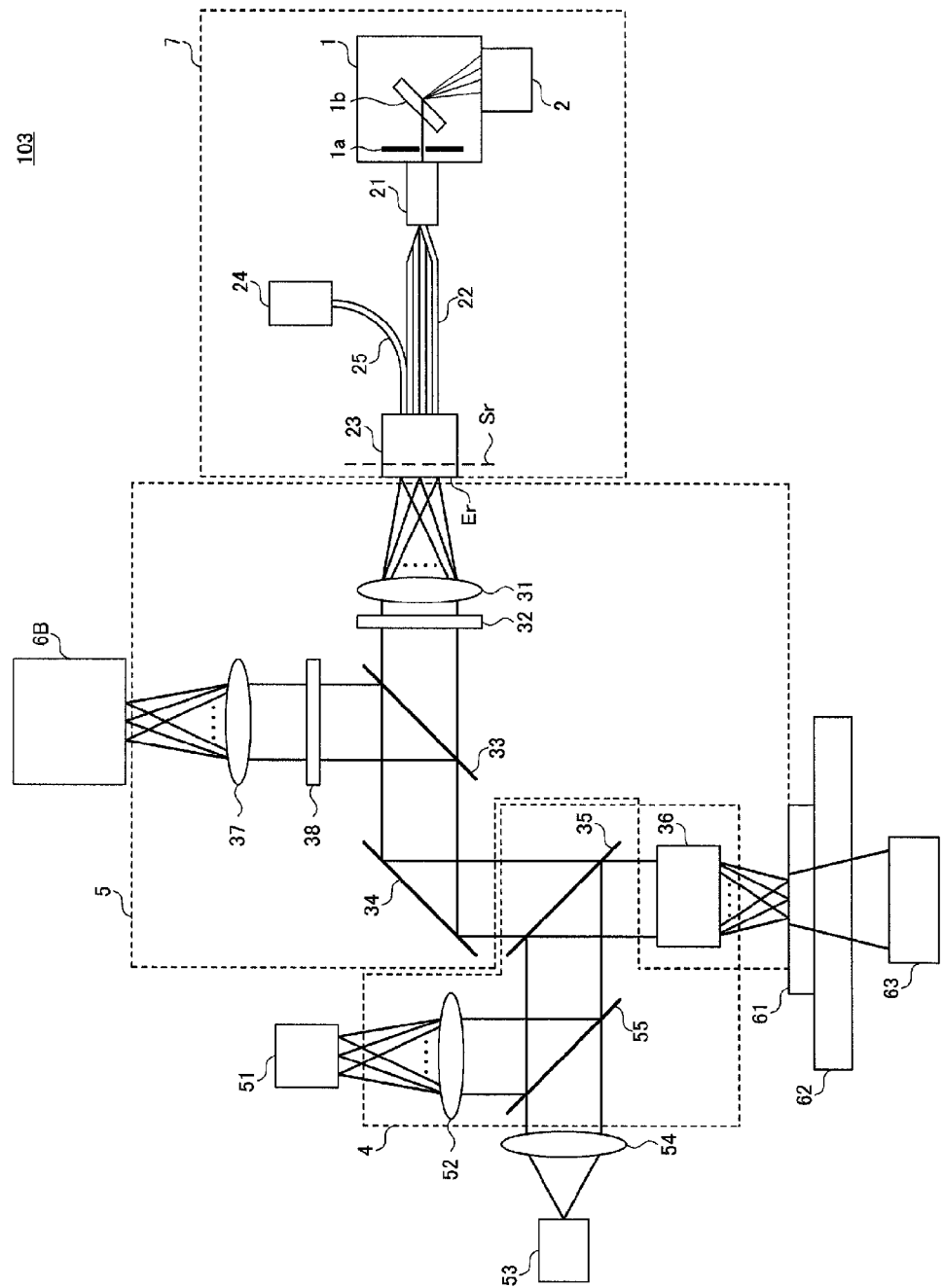
FIG. 11 is a view showing the configuration of a microspectroscope according to a third embodiment of the present invention.

FIG. 11 is a view showing the configuration of the microspectroscope according to the third embodiment of the present invention.

Referring to FIG. 11, a microspectroscope 103 includes the observation optical system 4, the confocal optical system 5, a light projecting portion 6B, the light receiving portion 7, the observation camera 51, the reflection illuminator 53, the collimating lens 54, the XYZ stage 62, and the transmission illuminator 63.

The functions of the observation optical system 4, the confocal optical system 5, the light receiving portion 7, the observation camera 51, the reflection illuminator 53, the collimating lens 54, the XYZ stage 62, and the transmission illuminator 63 in the microspectroscope 103 are respectively similar to those of the observation optical system 4, the confocal optical system 5, the light receiving portion 7, the observation camera 51, the reflection illuminator 53, the collimating lens 54, the XYZ stage 62, and the transmission illuminator 63 in the microspectroscope 101 shown in FIG. 1.

Figure 12:
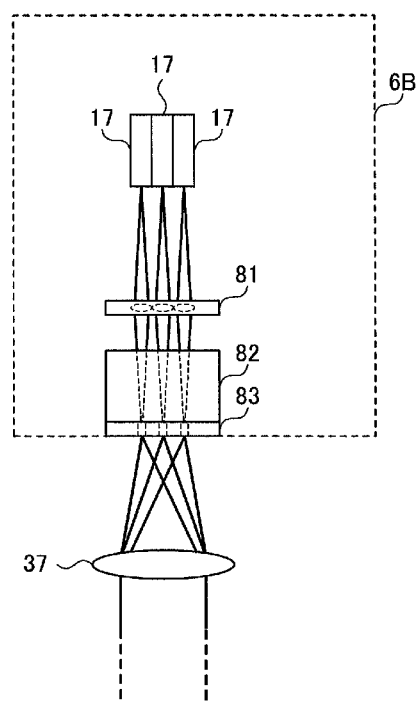
FIG. 12 is a view showing the configuration of a light projecting portion in the microspectroscope according to the third embodiment of the present invention.

FIG. 12 is a view showing the configuration of the light projecting portion in the microspectroscope according to the third embodiment of the present invention.

Referring to FIG. 12, the light projecting portion 6B includes the plurality of measurement light sources 17, a lens array 81, partition plates 82, and a pinhole plate 83.

Figure 13:
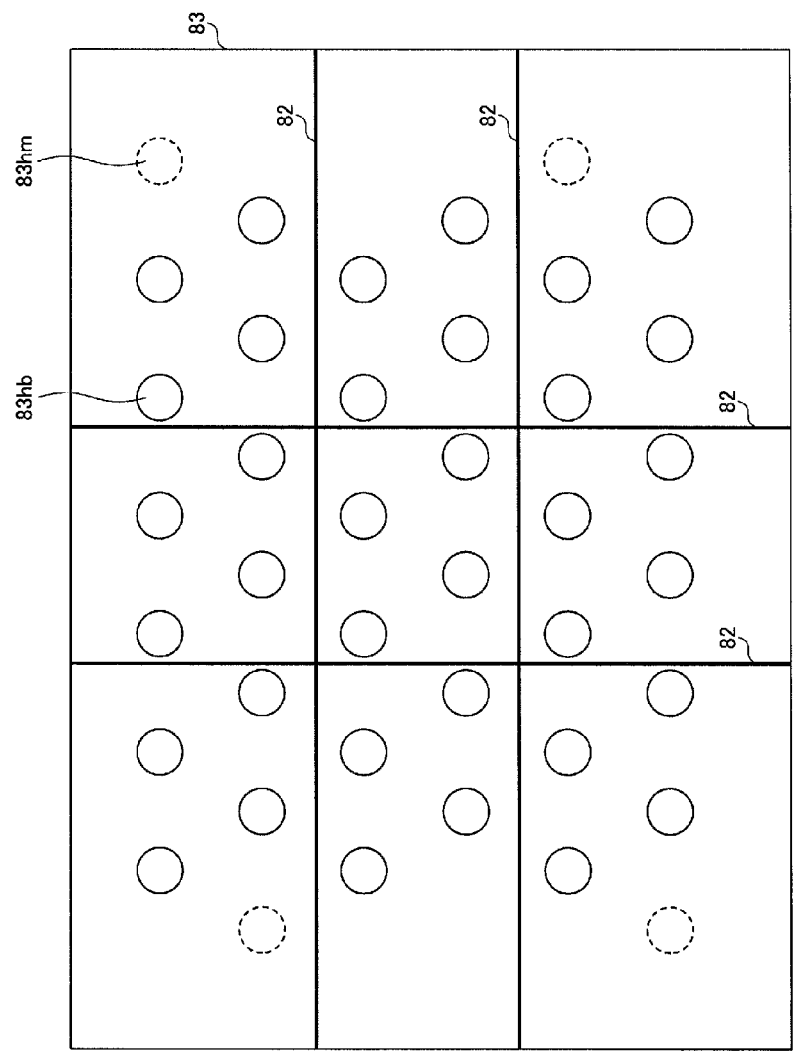
FIG. 13 is a plan view of a main surface of a pinhole plate shown in FIG. 12.

FIG. 13 is a plan view of a main surface of the pinhole plate shown in FIG. 12. In FIG. 13, projecting light generating holes 83*hb* and marker light generating holes 83*hm* are respectively represented by solid lines and broken lines.

Referring to FIGS. 12 and 13, the pinhole plate 83 is provided with, for example, 36 projecting light generating holes 83*hb* and four marker light generating holes 83*hm*. Each of the marker light generating holes 83*hm* has a diameter that is, for example, substantially the same as the diameter of each the projecting light generating holes 83*hb*.

The positions of the 36 projecting light generating holes 83*hb* and the four marker light generating holes 83*hm* are, for example, respectively the same as those of the 36 projecting light generating holes 40*hb* and the marker light generating holes 40*hm* of the pinhole plate 40 shown in FIG. 9.

The partition plates 82 extend, for example, from the pinhole plate 83 toward the measurement light sources 17, and divide the pinhole plate 83 into nine sub areas in a plan view in a direction that is along the propagation direction of the projecting light source. Each of the sub areas includes, for example, four projecting light generating holes 83*hb*. Furthermore, the sub areas at the four corners further include, for example, the marker light generating holes 83*hm* respectively.

The lens array 81 includes, for example, nine lenses that are provided so as to correspond to the sub areas of the pinhole plate 83.

The plurality of projecting light generating holes 83*hb* receive, for example, light from the plurality of measurement light sources 17. Each measurement light source 17 irradiates light, for example, onto one or a plurality of corresponding projecting light generating holes 83*hb*, which are part of the plurality of projecting light generating holes 83*hb*.

Specifically, the 36 projecting light generating holes 83*hb* receive, for example, light from nine measurement light sources 17. Each measurement light source 17 irradiates light, for example, onto four corresponding projecting light generating holes 83*hb*, which are part of the 36 projecting light generating holes 83*hb*.

The configuration of each measurement light source 17 is not limited to that in which it irradiates light onto four corresponding projecting light generating holes 83*hb*, which are part of the 36 projecting light generating holes 83*hb*, and a configuration is also possible in which the measurement light source 17 irradiates light onto three or less or five or more corresponding projecting light generating holes 83*hb*.

The optical paths of the light from the measurement light sources 17 are regulated, for example, such that light that is received by each projecting light generating hole 83*hb* is light from one corresponding measurement light source 17.

In other words, for example, the optical paths between the measurement light sources 17 and the projecting light generating holes 83*hb* are regulated such that light from one measurement light source 17 is irradiated onto one or a plurality of corresponding projecting light generating holes 83*hb*.

More specifically, nine measurement light sources 17 are provided, for example, so as to correspond to the sub areas of the pinhole plate 83.

Each lens of the lens array 81 condenses, for example, light spread apart from the corresponding measurement light source 17, onto the corresponding sub areas of the pinhole plate 83. At this time, the partition plates 82 prevent, for example, light from a measurement light source 17 from being irradiated onto sub areas other than the corresponding sub areas.

The 36 projecting light generating holes 83*hb* generate, for example, 36 light sources from light emitted from the measurement light sources 17 and condensed by the lens array 81, at the pinhole plate 83 on one side thereof that is farther from the measurement light sources 17 than the other side is.

In a similar manner, the four marker light generating holes 83hm generate, for example, four light sources from light emitted from the measurement light sources 17 and condensed by the lens array 81, at the pinhole plate 83 on one side thereof that is farther from the measurement light sources 17 than the other side is.

The collimating lens 37 converts, for example, light spread apart from the light sources generated by the projecting light generating holes 83hb, into a projecting beam group consisting of substantially parallel beams, and converts light spread apart from the light sources generated by the marker light generating holes 83hm, into a light projecting marker beam group consisting of substantially parallel beams.

The other aspects of the configuration and the other operations are similar to those of the microspectroscope 101 according to the first embodiment, and thus a detailed description thereof will not be repeated.

Next, another embodiment of the present invention will be described with reference to the drawings. Note that the same or corresponding constituent elements in the drawings are denoted by the same reference numerals, and a description thereof will not be repeated.

Fourth Embodiment

This embodiment relates to a microspectroscope that is different from the microspectroscope according to the first embodiment, in that it uses no optical fibers on the light projecting side and is of a transmission type. The microspectroscope is similar to that according to the first embodiment, except for the aspects that will be described below.

Figure 14:
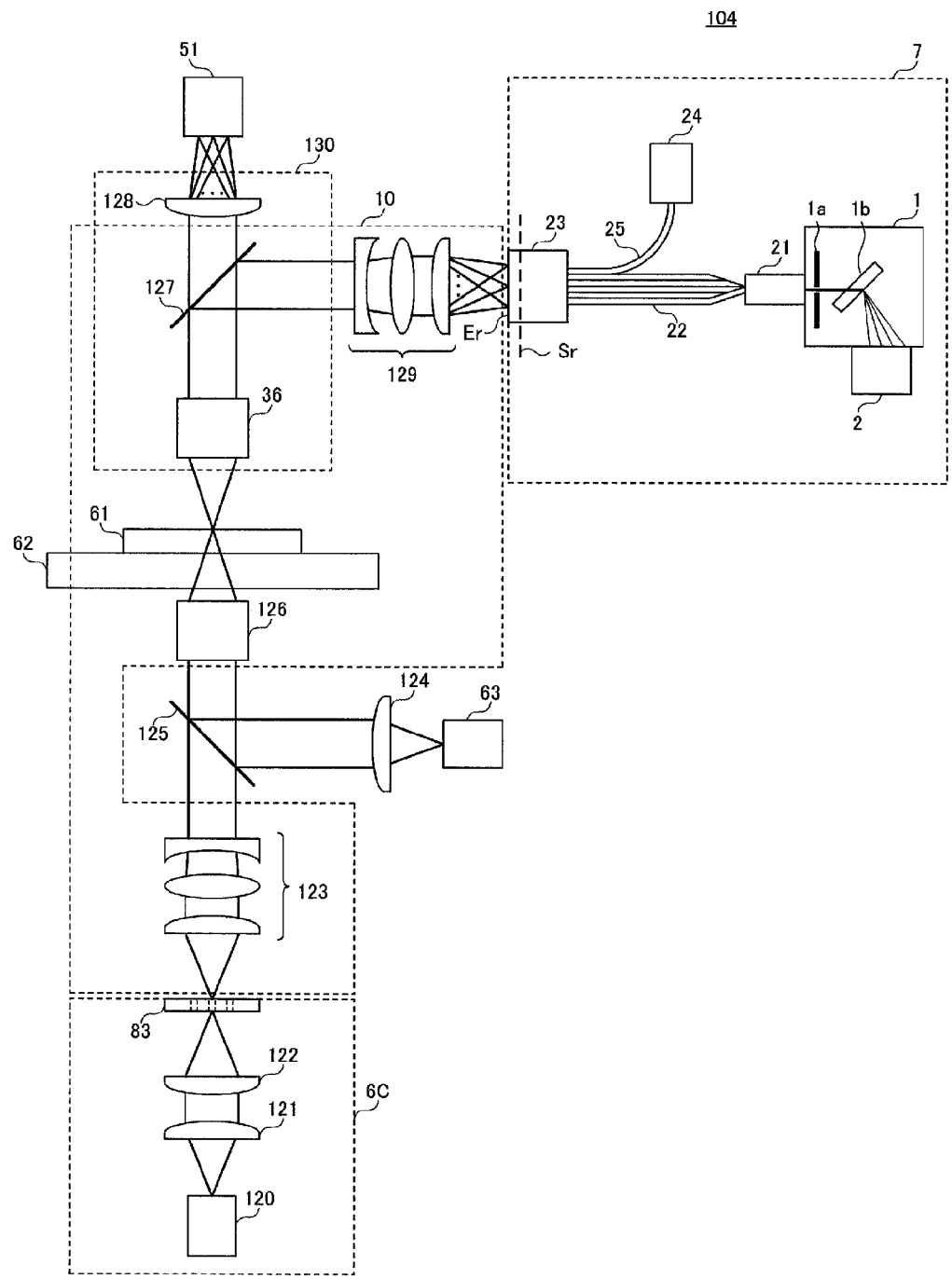
FIG. 14 is a view showing the configuration of a microspectroscope according to a fourth embodiment of the present invention.

FIG. 14 is a view showing the configuration of a microspectroscope according to the fourth embodiment of the present invention.

Referring to FIG. 14, a microspectroscope 104 includes a light projecting portion 6C, the light receiving portion 7, a confocal optical system 10, the observation camera 51, the XYZ stage 62, the transmission illuminator 63, a collimating lens 124, a half mirror 125, and an observation optical system 130.

The functions of the light receiving portion 7, the observation camera 51, the XYZ stage 62, and the transmission illuminator 63 in the microspectroscope 104 are respectively similar to those of the light receiving portion 7, the observation camera 51, the XYZ stage 62, and the transmission illuminator 63 in the microspectroscope 101 shown in FIG. 1.

The light projecting portion 6C includes the pinhole plate 83, a measurement light source 120, a collimating lens 121, and a condensing lens 122. The function of the pinhole plate 83 in the light projecting portion 6C is similar to that of the pinhole plate 83 in the light projecting portion 6B shown in FIG. 12.

The confocal optical system 10 includes a collimating lens group 123, an object lens 126, the object lens 36, a half mirror 127, and a condensing lens group 129. The observation optical system 130 includes the object lens 36 and an imaging lens 128.

The light projecting portion 6C generates, for example, light sources at multiple points. More specifically, the measurement light source 120 is, for example, an LED, an incandescent electric lamp, or the like. The measurement light source 120 may be a laser.

The collimating lens 121 converts light spread apart from the measurement light source 120, into projecting beams consisting of substantially parallel beams. The condensing lens 122 condenses each of the projecting beams from the collimating lens 121, on the pinhole plate 83.

The 36 projecting light generating holes 83hb of the pinhole plate 83 shown in FIG. 13 generate, for example, 36 light sources from light emitted from the measurement light source 120 and condensed by the condensing lens 122, at the pinhole plate 83 on one side thereof that is farther from the measurement light source 120 than the other side is.

In a similar manner, the four marker light generating holes 83hm generate, for example, four light sources from light emitted from the measurement light source 120 and condensed by the condensing lens 122, at the pinhole plate 83 on one side thereof that is farther from the measurement light source 120 than the other side is.

The confocal optical system 10 has a function of causing each of a plurality of beams formed by light from the measurement light source 120 to be condensed and irradiated onto the sample 61, and forming images of a plurality of beams from a plurality of condensing points on the sample 61, respectively on the plurality of light receiving optical fibers 22.

More specifically, the collimating lens group 123 converts, for example, light spread apart from the light sources generated by the projecting light generating holes 83hb, into a projecting beam group consisting of substantially parallel beams, and converts light spread apart from the light sources generated by the marker light generating holes 83hm, into a light projecting marker beam group consisting of substantially parallel beams.

The object lens 126 condenses, for example, each of a plurality of beams contained in the projecting beam group and the light projecting marker beam group from the collimating lens group 123, on the sample 61.

On the sample 61, for example, real images RIpt that are similar to the real images RIp shown in FIG. 4 are formed. In this example, the real images RIpt are, for example, real images of the 36 projecting light generating holes 83hb of the pinhole plate 83, generated by causing each of beams from the projecting light generating holes 83hb to be condensed on the sample 61 by the confocal optical system 10.

In a similar manner, on the sample 61, for example, real images RIpmt that are similar to the real images RIpm shown in FIG. 4 are formed. In this example, the real images RIpmt are, for example, real images of the four marker light generating holes 83hm of the pinhole plate 83, generated by causing each of beams from the marker light generating holes 83hm to be condensed on the sample 61 by the confocal optical system 10.

The object lens 36 converts, for example, light spread apart from the real images RIpt, into a receiving beam group consisting of substantially parallel beams.

The half mirror 127 reflects, for example, part of the receiving beam group converted by the object lens 36.

The condensing lens group 129 condenses, for example, a plurality of beams contained in the receiving beam group reflected by the half mirror 127, respectively on the cores 22a of the corresponding light receiving optical fibers 22.

Furthermore, for example, the confocal optical system 10 causes each of the marker beams from the light receiving marker optical fibers 25 to be condensed and irradiated onto the sample 61.

More specifically, the condensing lens group 129 converts, for example, light spread apart from the output ends of the light receiving marker optical fibers 25, into a light receiving marker beam group consisting of substantially parallel beams.

The light receiving marker beam group is, for example, reflected by the half mirror 127, and is incident on the object lens 36.

The object lens 36 condenses, for example, each of a plurality of beams contained in the light receiving marker beam group reflected by the half mirror 127, on the sample 61.

On the sample 61, for example, real images RIrmt that are similar to the real images RIrm shown in FIG. 4 are formed.

For example, when observing the sample 61 in a transmission mode, the transmission illuminator 63 irradiates light onto the sample 61 from the side that is farther from the object lens 36 than the sample 61 is. More specifically, the half mirror 125 reflects, for example, beams emitted from the transmission illuminator 63 and collimated by the collimating lens 124, thereby guiding the beams via the object lens 126 to irradiate the sample 61.

The observation optical system 130 condenses, for example, each of beams from the condensing points on the sample 61, on the observation camera 51.

More specifically, the object lens 36 in the observation optical system 130 collimates, for example, light spread apart from the sample 61. The imaging lens 128 condenses, for example, light collimated by the object lens 36 and partially transmitted through the half mirror 127, on the observation camera 51.

For example, the observation camera 51 generates an image containing the real images RIpt, RIrmt, and RIpmt on the sample 61 based on the light from the sample 61 condensed by the observation optical system 130.

For example, the microspectroscope 104 can measure the spectral transmittance of pixels of a color filter contained in a flat panel display. At this time, the microspectroscope 104 can simultaneously measure, for example, the spectral transmittances of a plurality of pixels.

Although the configuration was described in which the microspectroscope according to the fourth embodiment of the present invention includes the light projecting portion 6C, there is no limitation to this. The microspectroscope 104 may be configured so as to include the light projecting portion 6, the light projecting portion 6A, or the light projecting portion 6B, instead of the light projecting portion 6C.

The other aspects of the configuration and the other operations are similar to those of the microspectroscope 101 according to the first embodiment, and thus a detailed description thereof will not be repeated.

Note that part or the whole of the constituent elements and the operations of the devices according to the first to fourth embodiments of the present invention may be combined as appropriate.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A microspectroscope, comprising:
    a plurality of light sources;
    a plurality of light projecting optical fibers that receive light from the plurality of light sources;
    a spectroscope;
    a plurality of light receiving optical fibers for guiding received light to the spectroscope; and
    a confocal optical system for causing each of a plurality of beams from the plurality of light projecting optical fibers to be condensed and irradiated onto a sample, and forming images of a plurality of beams from a plurality of condensing points on the sample, respectively on the plurality of light receiving optical fibers, wherein
    the plurality of light projecting optical fibers receive light from the plurality of light sources,
    each of the light sources of the plurality of light sources irradiates light onto one or a plurality of corresponding light projecting optical fibers, which are part of the plurality of light projecting optical fibers, and
    optical paths of light from the plurality of light sources are regulated such that light that is received by each light projecting optical fiber is light from only one corresponding light source of the plurality of light sources.

2. The microspectroscope according to claim 1, wherein the plurality of light projecting optical fibers and the plurality of light receiving optical fibers are individually two-dimensionally arranged, and
    at least either the plurality of light projecting optical fibers or the plurality of light receiving optical fibers are arranged closer to each other than in a state in which the optical fibers are arranged in contact with each other in a square lattice, in a cross-section cut along a plane that is orthogonal to an extending direction of the optical fibers.

3. The microspectroscope according to claim 1, wherein the microspectroscope further comprises:
    a light projecting marker optical fiber that is fixed along the plurality of light projecting optical fibers and that receives light from another light source that either is at least one of the plurality of light source or is different from the plurality of light sources, on an input end side of the light projecting optical fibers; and
    a light receiving marker optical fiber that is fixed along the plurality of light receiving optical fibers and that receives light from a further light source that is different from the plurality of light sources, on an output end side of the light receiving optical fibers, and
    the confocal optical system causes each of a marker beam from the light projecting marker optical fiber and a marker beam from the light receiving marker optical fiber to be condensed and irradiated onto a sample.

4. The microspectroscope according to claim 3, wherein the microspectroscope further comprises:
    a light projecting marker light source; and
    a light receiving marker light source;
    the light projecting marker optical fiber receives light from the light projecting marker light source, on an input end side of the light projecting optical fibers, the light receiving marker optical fiber receives light from the light receiving marker light source, on an output end side of the light receiving optical fibers, and
    the light projecting marker light source and the light receiving marker light source output light having mutually different colors.

5. The microspectroscope according to claim 1, wherein an outer diameter of a core of each of the light receiving optical fibers is larger than an outer diameter of a 10 core of each of the light projecting optical fibers.

6. A microspectroscope, comprising:
    a plurality of light sources;
    a spectroscope;
    a plurality of light receiving optical fibers that are two-dimensionally arranged, for guiding received light to the spectroscope; and a confocal optical system for causing each of a plurality of beams formed by light from the plurality of light sources to be condensed and irradiated onto a sample, and forming images respectively on the plurality of light receiving optical fibers, wherein the images are images of a plurality of beams from a plurality of condensing points on the sample, wherein the plurality of light receiving optical fibers are two-dimensionally arranged, and are arranged closer to each other than in a state in which the optical fibers are arranged in contact with each other in a square lattice, in a cross-section cut along a plane that is orthogonal to an extending direction of the optical fibers, the microspectroscope further comprises a plurality of light receiving marker optical fibers that are fixed along the plurality of light receiving optical fibers and that receive light from another light source that either is at least one of the plurality of light sources or is different from the plurality of light sources, on an output end side of the light receiving optical fibers, the confocal optical system causes each of a plurality of marker beams from the plurality of light receiving marker optical fibers to be condensed and irradiated onto the sample, the confocal optical system includes a pinhole plate which is provided with projecting light generating holes and which receive light from the plurality of light sources, each of the plurality of light sources irradiates light onto one or a plurality of corresponding projecting light generating holes, which are part of the plurality of projecting light generating holes of the pinhole plate, and optical paths of light from the plurality of light sources are regulated such that light that is received by each light generating hole is light from only one corresponding light source of the plurality of light sources.

\* \* \* \* \*